(12) United States Patent
Rigo

(10) Patent No.: US 10,793,855 B2
(45) Date of Patent: Oct. 6, 2020

(54) COMPOSITIONS FOR MODULATING EXPRESSION OF C9ORF72 ANTISENSE TRANSCRIPT

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/540,251

(22) PCT Filed: Jan. 6, 2016

(86) PCT No.: PCT/US2016/012381
§ 371 (c)(1),
(2) Date: Jun. 27, 2017

(87) PCT Pub. No.: WO2016/112132
PCT Pub. Date: Jul. 14, 2016

(65) Prior Publication Data
US 2018/0023077 A1  Jan. 25, 2018

Related U.S. Application Data

(60) Provisional application No. 62/100,439, filed on Jan. 6, 2015, provisional application No. 62/148,621, filed on Apr. 16, 2015, provisional application No. 62/148,657, filed on Apr. 16, 2015.

(51) Int. Cl.
| | | |
|---|---|---|
| *C07H 21/04* | (2006.01) | |
| *C12N 15/113* | (2010.01) | |
| *A61K 45/06* | (2006.01) | |
| *A61K 31/7125* | (2006.01) | |
| *A61K 31/712* | (2006.01) | |
| *A61K 9/00* | (2006.01) | |
| *A61K 31/713* | (2006.01) | |

(52) U.S. Cl.
CPC .......... *C12N 15/113* (2013.01); *A61K 9/0085* (2013.01); *A61K 31/712* (2013.01); *A61K 31/713* (2013.01); *A61K 31/7125* (2013.01); *A61K 45/06* (2013.01); *C12N 2310/11* (2013.01); *C12N 2310/14* (2013.01); *C12N 2310/31* (2013.01); *C12N 2310/315* (2013.01); *C12N 2310/321* (2013.01); *C12N 2310/322* (2013.01); *C12N 2310/3231* (2013.01); *C12N 2310/33* (2013.01); *C12N 2310/3341* (2013.01); *C12N 2310/341* (2013.01); *C12N 2310/346* (2013.01); *C12N 2310/351* (2013.01); *C12N 2320/31* (2013.01)

(58) Field of Classification Search
CPC ..................................................... C07H 21/04
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler |
| 5,214,134 A | 5/1993 | Weis et al. |

(Continued)

FOREIGN PATENT DOCUMENTS

| | | |
|---|---|---|
| WO | WO 2002/062954 | 8/2002 |
| WO | WO 2005/063976 | 7/2005 |

(Continued)

OTHER PUBLICATIONS

Ash et al., "Unconventional translation of C9ORF72 GGGGCC expansion generates insoluble polypeptides specifict to c9FTD/ASL." Neuron (2013) 77(4):639-646.

Baughn et al, "Sense and Anti-Sense RNA Foci in c9 ALS/FTD: More Light in a House of Mirrors" Annals of Neurology (Oct. 14, 2013) 74(17): pS60.

Blitterswijk et al., "How do C9ORF72 repeat expansions cause amyotrophic lateral sclerosis and frontotemporal dementia: can we learn from other noncoding repeat expansion disorders?" Curr Opin Neurol. (2012) 25(6):689-700.

(Continued)

*Primary Examiner* — Kimberly Chong
(74) *Attorney, Agent, or Firm* — McNeill Baur PLLC

(57) ABSTRACT

Disclosed herein are compositions and methods for reducing expression of C9ORF72 antisense transcript in an animal with C9ORF72 antisense transcript specific inhibitors. Such methods are useful to treat, prevent, or ameliorate neurodegenerative diseases in an individual in need thereof. Such C9ORF72 antisense transcript specific inhibitors include antisense compounds.

42 Claims, No Drawings
Specification includes a Sequence Listing.

(56) References Cited

U.S. PATENT DOCUMENTS

| | | |
|---|---|---|
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,372,492 B1 | 4/2002 | Bennett et al. |
| 6,426,220 B1 | 7/2002 | Bennett et al. |
| 6,525,191 B1 | 2/2003 | Ramasamy |
| 6,531,584 B1 | 3/2003 | Cook et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,833,361 B2 * | 12/2004 | Hong .................... C07H 19/04 514/45 |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,410,070 B2 | 4/2013 | Miller et al. |
| 8,440,803 B2 | 5/2013 | Swayze et al. |
| 8,501,805 B2 | 8/2013 | Seth et al. |
| 8,530,640 B2 | 9/2013 | Seth et al. |

(56) References Cited

U.S. PATENT DOCUMENTS

| | | | |
|---|---|---|---|
| 8,546,556 | B2 | 10/2013 | Seth et al. |
| RE44,779 | E | 2/2014 | Imanishi et al. |
| 8,828,956 | B2 | 9/2014 | Manoharan et al. |
| 9,005,906 | B2 | 4/2015 | Swayze et al. |
| 9,012,421 | B2 | 4/2015 | Migawa et al. |
| 9,127,276 | B2 | 8/2015 | Prakash et al. |
| 9,290,760 | B2 | 3/2016 | Rajeev et al. |
| 10,174,323 | B2 * | 1/2019 | Krieg .................... C07H 21/00 |
| 10,407,678 | B2 | 9/2019 | Rigo |
| 2003/0082807 | A1 | 5/2003 | Wengel |
| 2003/0158403 | A1 | 8/2003 | Manoharan et al. |
| 2003/0175906 | A1 | 9/2003 | Manoharan et al. |
| 2003/0207841 | A1 | 11/2003 | Kaneko et al. |
| 2003/0224377 | A1 | 12/2003 | Wengel et al. |
| 2004/0143114 | A1 | 7/2004 | Imanishi et al. |
| 2004/0171570 | A1 | 9/2004 | Allerson et al. |
| 2004/0192918 | A1 | 9/2004 | Imanishi et al. |
| 2004/0265230 | A1 | 12/2004 | Martinez et al. |
| 2005/0130923 | A1 | 6/2005 | Bhat et al. |
| 2005/0255487 | A1 * | 11/2005 | Khvorova ............ A61K 31/713 |
| | | | 435/6.11 |
| 2006/0148740 | A1 | 7/2006 | Platenburg |
| 2006/0286575 | A1 | 12/2006 | Farrell et al. |
| 2008/0039618 | A1 | 2/2008 | Allerson et al. |
| 2010/0190837 | A1 | 7/2010 | Migawa et al. |
| 2010/0197762 | A1 | 8/2010 | Swayze et al. |
| 2011/0123520 | A1 | 5/2011 | Manoharan et al. |
| 2011/0294870 | A1 | 12/2011 | Collard et al. |
| 2013/0130378 | A1 | 5/2013 | Manoharan et al. |
| 2013/0203836 | A1 | 8/2013 | Rajeev et al. |
| 2014/0107330 | A1 | 4/2014 | Freier et al. |
| 2014/0303238 | A1 | 10/2014 | Linsley |
| 2015/0018540 | A1 | 1/2015 | Prakash et al. |
| 2015/0141320 | A1 * | 5/2015 | Krieg .................. A61K 31/7088 |
| | | | 514/1.1 |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0267197 | A1 | 9/2015 | Bennett et al. |
| 2015/0275212 | A1 | 10/2015 | Albaek et al. |
| 2016/0025747 | A1 | 1/2016 | Ranum et al. |
| 2016/0108396 | A1 | 4/2016 | Jensen et al. |
| 2016/0230172 | A1 | 8/2016 | Rigo |
| 2016/0237432 | A1 | 8/2016 | Bennett et al. |
| 2018/0016575 | A1 * | 1/2018 | Hansen .................. C07H 21/00 |
| 2018/0119142 | A1 | 5/2018 | Rigo |
| 2018/0142240 | A1 | 5/2018 | Bennett et al. |

FOREIGN PATENT DOCUMENTS

| | | |
|---|---|---|
| WO | WO 2007/056113 | 5/2007 |
| WO | WO 2012/114111 | 8/2012 |
| WO | WO 2014/062691 | 4/2014 |
| WO | WO 2015/057727 | 4/2015 |
| WO | WO 2015/057738 | 4/2015 |
| WO | WO 2016/112132 | 7/2016 |
| WO | WO 2016/167780 | 10/2016 |

OTHER PUBLICATIONS

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciura et al., "Loss of function of C9orf72 causes motor deficits in a zebrafish model of Amyotrophic Lateral Sclerosis" Annals of Neurology (2013).

Cleveland, D.W., "Gene silencing therapy for human neurodegenerative disease" Oral Presentation, 10th Brain Research Conference, Chicago, IL, Oct. 15, 2015.

Crooke, ST., et al., "Antisense Drug Technology" Second Edition, CRC Press (2008) Chapters 1-28.

Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Extended European Search Report for Application No. 14854291.3 dated Apr. 24, 2017.

Extended European Search Report for Application No. 14854442.2 dated May 17, 2017.

Gautschi et al., "Activity of a novel bcl-2/bcl-xLbispecific antisense oligonucleotide against tumors of diverse histologic origins" J. Natl. Cancer Inst. (2001) 93:463-471.

Gendron et al., "Antisense transcripts of the expanded C9ORF72 hexanucleotide repeat form nuclear RNA foci and undergo repeat-associated non-ATG translation in c9FTD/ALS." Acta Nuropathol (2013) 126(6):829-844.

Gendron et al., "c9RAN Translation: a potential therapeutic target for the treatment of amyotrophic lateral sclerosis and frontotemporal dementia." Expert Opin. Ther. Targets (2013) 17(9):991-995.

Gendron et al., "Disease Mechanisms of C9ORF72 Repeat Expansions" Cold Spring Harbor Perspect Med (Jan. 27, 2017) soi: 10.1101/schperspec.a024224.

Hirtz et al., "How common are the "common" neurologic disorders?" Neurology (2007) 68:326-337.

International Search Report for application No. PCT/US2014/060512 dated Jan. 21, 2015.

International Search Report for application No. PCT/US2014/060530 dated Jan. 21, 2015.

International Search Report for application No. PCT/US2015/026218 dated Oct. 23, 2015.

International Search Report for application No. PCT/US2016/012381 dated May 17, 2016.

Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.

Jiang et al., "Bidirectional Transcriptinal Inhibition as Therapy for ALS/FTD Caused by Repeat Expanson in C9orf72" Neuron (2016) 92:1160-1163.

Johnson et al., "Exome sequencing reveals VCP mutations as a cause of familial ALS" Neuron (2010) 68:857-864.

Kwiatkowski et al., "Mutations in the FUS/TLS gene on chromosome 16 cause familial amyotrophic lateral sclerosis" Science (2009) 323:1205-1208.

Laaksovirta et al, "Chromosome 9p21 in amyotrophic lateral sclerosis in Finland: a genome-wide association study" Lancet Neurol. (2010) 9:978-985.

Lagier-Tourenne C, et al. "Targeted degradation of sense and antisense C9orf72 RNA foci as therapy for ALS and frontotemporal degeneration" PNAS (2013) 110(47):E4530-E4539.

Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.

Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.

Lillo et al., "Frontotemporal dementia and motor neurone disease: overlapping clinic-pathological disorders" J. Clin. Neurosci. (2009) 16:1131-1135.

Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.

Maruyama et al., "Mutations of optineurin in amyotrophic lateral sclerosis" Nature (2010) 465:223-226.

Mori et al., "The C9orf72 GGGGCC repeat is translated into aggregating dipeptide-repeat proteins in FTLD/ALS." Science (2013) 339:1335-1338.

(56) References Cited

OTHER PUBLICATIONS

Mori et al., Supplemental Material for "The C9orf72 GGGGCC repeat is translated into aggregating dipeptide-repeat proteins in FTLD/ALS." Science (2013) 339:1335-1338.
Morita et al., "A locus on chromosome 9p confers susceptibility to ALS and frontotemporal dementia" Neurology (2006) 66:839-844.
Mulders et al. "Triplet-repeat oligonucleotide-mediated reversal of RNA toxicity in myotonic dysrophy." Proc. Nat. Acad. Sci. USA (2009) 106(33):13915-13920.
NCBI Reference AC255463 *Homo sapiens* crhromosome 9 clone 174779_ABC12_000049116500_D6. (Jul. 16, 2014) [Retreived from the internet Aug. 17, 2016: <http://www.ncbi.nlm.nih.gov/nuccore/AC255463.1>].
Neumann et al., "Ubiquitinated TDP-43 in frontotemporal lobar degeneration and amyotrophic lateral sclerosis" Science (2006) 314:130-133.
Pearson et al., "Familial frontotemporal dementia with amyotrophic lateral sclerosis and a shared haplotype on chromosome 9p" J. Nerol. (2011) 258:647-655.
Picher-Martel et al., "From Animal Models to Human Disease: A Genetic Approach for Personalized Medicine in ALS" Acta Neuropathologica Communications (2016) 4(70): 1-29.
Renton et al., "A hexanucleotide repeat expansion in C9orf72 is the cause of chromosome 9p21-linked ASL-FTD." Neuron (2011) 72(2):257-268.
Riboldi et al., "Antisense oligonucleotide therapy for the treatment of C9ORF72 ALS/FTD diseases." Mol Nuerobiol (2014) 50(3):721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.

Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sareen et al., "Targeting RNA foci in iPSC-derived motor neurons from ALS patients with a C9ORF72 repeat expansion." Sci Tran Med (2013) 5(208): 1-13.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Sha et al., "Treatment implications of C9ORF72" Alzheimers Res Ther (2012) 4(6): 46.
Sreedharan et al., "TDP-43 mutations in familial and sporadic amyotrophic lateral sclerosis" Science (2008) 319:1668-1672.
Todd et al, "RNA-Mediated Neurodegeneration in Repeat Expansion Disorders." Annals of Neurology (2010) 67:291-300.
Vance et al., "Familial amyotrophic lateral sclerosis with frontotemporal dementia is linked to a locus on chromosome 9p13.2-21.3" Brain (2006) 129:868-876.
Woolf et al., "Specificity of antisense oligonucleotides in vivo" PNAS (1992) 89: 7305-7309.
Xu et al., "Expanded GGGGCC repeat RNA associated with amyotrophic lateral sclerosis and frontotemporal dementia causes neurodegeneration" Proceedings National Academy of Sciences PNAS (2013) 110(19): 7778-7783.
Zu et al., "RNA proteins and RNA foci from antisense transcripts in C9ORF72 ALS and frontotemoral," PNAS (2013) E4968-E4977.

* cited by examiner

COMPOSITIONS FOR MODULATING EXPRESSION OF C9ORF72 ANTISENSE TRANSCRIPT

SEQUENCE LISTING

The present application is being filed along with a Sequence Listing in electronic format. The Sequence Listing is provided as a file entitled BIOL0262USASEQ_ST25.txt created Jun. 27, 2017 Jan. 5, 2016, which is 76 Kb in size. The information in the electronic format of the sequence listing is incorporated herein by reference in its entirety.

FIELD

Provided are compositions and methods for inhibiting expression of C9ORF72 antisense transcript in an animal. Such compositions and methods are useful to treat, prevent, or ameliorate neurodegenerative diseases, including amyotrophic lateral sclerosis (ALS), frontotemporal dementia (FTD), corticobasal degeneration syndrome (CBD), atypical Parkinsonian syndrome, and olivopontocerebellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). This mutation has been found to be the most common genetic cause of ALS and FTD. It is postulated that the ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

There are currently no effective therapies to treat such neurodegenerative diseases. Therefore, it is an object to provide compositions and methods for the treatment of such neurodegenerative diseases.

SUMMARY

Provided herein are compositions and methods for modulating levels of C9ORF72 antisense transcript in cells, tissues, and animals. In certain embodiments, C9ORF72 antisense transcript specific inhibitors modulate expression of C9ORF72 antisense transcript. In certain embodiments, C9ORF72 antisense transcript specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 antisense transcript levels are reduced. In certain embodiments, C9ORF72 antisense transcript associated RAN translation products are reduced. In certain embodiments, the C9ORF72 antisense transcript associated RAN translation products are poly-(proline-alanine), poly-(proline-arginine), and poly-(proline-glycine). In certain embodiments, the C9ORF72 antisense transcript contains a hexanucleotide repeat expansion. In certain embodiments, the hexanucleotide repeat is transcribed in the antisense direction from the C9ORF72 gene. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGCCCC, CCCCCC, GCCCCC, and/or CGCCCC repeats. In certain embodiments, the hexanucleotide repeat expansion comprises more than 30 GGCCCC, CCCCCC, GCCCCC, and/or CGCCCC repeats. In certain embodiments, the hexanucleotide repeat expansion comprises more than 100 GGCCCC, CCCCCC, GCCCCC, and/or CGCCCC repeats. In certain embodiments, the hexanucleotide repeat expansion comprises more than 500 GGCCCC, CCCCCC, GCCCCC, and/or CGCCCC repeats. In certain embodiments, the hexanucleotide repeat expansion comprises more than 1000 GGCCCC, CCCCCC, GCCCCC, and/or CGCCCC repeats. In certain embodiments, the hexanucleotide repeat expansion is associated with nuclear foci. In certain embodiments, C9ORF72 antisense transcript associated RAN translation products are associated with nuclear foci. In certain embodiments, the antisense transcript associated RAN translation products are poly-(proline-alanine) and/or poly-(proline-arginine). In certain embodiments, the compositions and methods described herein are useful for reducing C9ORF72 antisense transcript levels, C9ORF72 antisense transcript associated RAN translation products, and nuclear foci. Such reduction can occur in a time-dependent manner or in a dose-dependent manner.

Also provided are methods useful for preventing, treating, ameliorating, and slowing progression of diseases and conditions associated with C9ORF72. In certain embodiments, such diseases and conditions associated with C9ORF72 are neurodegenerative diseases. In certain embodiments, the neurodegenerative disease is amyotrophic lateral sclerosis (ALS), frontotemporal dementia (FTD), corticobasal degeneration syndrome (CBD), atypical Parkinsonian syndrome, and olivopontocerebellar degeneration (OPCD).

Such diseases and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 antisense transcript specific inhibitor to an individual in need thereof. In certain embodiments, the C9ORF72 antisense transcript specific inhibitor is a nucleic acid. In certain embodiments, the nucleic acid is an antisense compound. In certain embodiments, the antisense compound is an antisense oligonucleotide. In certain embodiments, the antisense oligonucleotide is complementary to a C9ORF72 antisense transcript. In certain embodiments, the antisense oligonucleotide is a modified antisense oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a MOE modified sugar moiety.

"2'-substituted nucleoside" means a nucleoside comprising a substituent at the 2'-position of the furanose ring other than H or OH. In certain embodiments, 2'-substituted nucleosides include nucleosides with bicyclic sugar modifications.

"5-methylcytosine" means a cytosine modified with a methyl group attached to the 5' position. A 5-methylcytosine is a modified nucleobase.

"About" means within +7% of a value. For example, if it is stated, "the compounds affected at least about 70% inhibition of C9ORF72 antisense transcript", it is implied that the C9ORF72 antisense transcript levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein product encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 antisense transcript" means transcripts produced from the non-coding strand (also antisense strand and template strand) of the C9ORF72 gene. The C9ORF72 antisense transcript differs from the canonically transcribed "C9ORF72 sense transcript", which is produced from the coding strand (also sense strand) of the C9ORF72 gene.

"C9ORF72 antisense transcript associated RAN translation products" means aberrant peptide or di-peptide polymers translated through RAN translation (i.e., repeat-associated, and non-ATG-dependent translation). In certain embodiments, the C9ORF72 antisense transcript associated RAN translation products are any of poly-(proline-alanine), poly-(proline-arginine), and poly-(proline-glycine).

"C9ORF72 antisense transcript specific inhibitor" refers to any agent capable of specifically inhibiting the expression of C9ORF72 antisense transcript and/or its expression products at the molecular level. As used herein, "specific" means reducing or inhibiting expression of C9ORF72 antisense transcript without reducing non-target transcript to an appreciable degree (e.g., a C9ORF72 antisense transcript specific inhibitor reduces expression of C9ORF72 antisense transcript, but does not reduce expression of C9ORF72 sense transcript to an appreciable degree).

C9ORF72 specific antisense transcript inhibitors include nucleic acids (including antisense compounds), siRNAs, aptamers, antibodies, peptides, small molecules, and other agents capable of inhibiting the expression of C9ORF72 antisense transcript and/or its expression products, such as C9ORF72 antisense transcript associated RAN translation products.

"C9ORF72 associated disease" means any disease associated with any C9ORF72 nucleic acid or expression product thereof, regardless of which DNA strand the C9ORF72 nucleic acid or expression product thereof is derived from. Such diseases may include a neurodegenerative disease. Such neurodegenerative diseases may include ALS and FTD.

"C9ORF72 foci" means nuclear foci comprising a C9ORF72 transcript. In certain embodiments, a C9ORF72 foci comprises at least one C9ORF72 sense transcript (herein "C9ORF72 sense foci"). In certain embodiments, C9ORF72 sense foci comprise C9ORF72 sense transcripts comprising any of the following hexanucleotide repeats: GGGGCC, GGGGGG, GGGGGC, and/or GGGGCG. In certain embodiments, a C9ORF72 foci comprises at least one C9ORF72 antisense transcript (herein "C9ORF72 antisense foci"). In certain embodiments, C9ORF72 antisense foci comprise C9ORF72 antisense transcripts comprising any of the following hexanucleotide repeats: GGCCCC, CCCCCC, GCCCCC, and/or CGCCCC. In certain embodiments, C9ORF72 foci comprise both C9ORF72 sense transcripts and C9ORF72 antisense transcripts.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise any of the following hexanucleotide repeats: GGGGCC, GGGGGG, GGGGGC, GGGGCG, GGCCCC, CCCCCC, GCCCCC, and/or CGCCCC. In certain embodiments, the hexanucleotide repeat is repeated at least 30 times, more than 30 times, more than 100 times, more than 500 times, or more than 1000 times. Such diseases may include a neurodegenerative disease. Such neurodegenerative diseases may include ALS and FTD.

"C9ORF72 nucleic acid" means any nucleic acid derived from the C9ORF72 locus, regardless of which DNA strand the C9ORF72 nucleic acid is derived from. In certain embodiments, a C9ORF72 nucleic acid includes a DNA sequence encoding C9ORF72, an RNA sequence transcribed from DNA encoding C9ORF72 including genomic DNA comprising introns and exons (i.e., pre-mRNA), and an mRNA sequence encoding C9ORF72. "C9ORF72 mRNA" means an mRNA encoding a C9ORF72 protein. In certain embodiments, a C9ORF72 nucleic acid includes transcripts produced from the coding strand of the C9ORF72 gene. C9ORF72 sense transcripts are examples of C9ORF72 nucleic acids. In certain embodiments, a C9ORF72 nucleic acid includes transcripts produced from the non-coding strand of the C9ORF72 gene. C9ORF72 antisense transcripts are examples of C9ORF72 nucleic acids.

"C9ORF72 pathogenic associated mRNA variant" means the C9ORF72 mRNA variant processed from a C9ORF72 pre-mRNA variant containing the hexanucleotide repeat. A C9ORF72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). In certain embodiments, the level of a C9ORF72 pathogenic associated mRNA variant is measured to determine the level of a C9ORF72 pre-mRNA containing the hexanucleotide repeat in a sample.

"C9ORF72 transcript" means an RNA transcribed from C9ORF72. In certain embodiments, a C9ORF72 transcript is a C9ORF72 sense transcript. In certain embodiments, a C9ORF72 transcript is a C9ORF72 antisense transcript.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information, regardless of which DNA strand the coded information is derived from, is converted into structures present and operating in a cell. Such structures include, but are not limited to the products of transcription and translation, including RAN translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" means a series of six bases (for example, GGGGCC, GGGGGG, GGGGGC, GGGGCG, GGCCCC, CCCCCC, GCCCCC, and/or CGCCCC) repeated at least twice. In certain embodiments, the hexanucleotide repeat expansion may be located in intron 1 of a C9ORF72 nucleic acid. In certain embodiments, the hexanucleotide repeat may be transcribed in the antisense direction from the C9ORF72 gene. In certain embodiments, a pathogenic hexanucleotide repeat expansion includes more than 30, more than 100, more than 500, or more than 1000 repeats of GGGGCC, GGGGGG, GGGGGC, GGGGCG, GGCCCC, CCCCCC, GCCCCC, and/or CGCCCC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 30 or fewer repeats of GGGGCC, GGGGGG, GGGGGC, GGGGCG, GGCCCC, CCCCCC, GCCCCC, and/or CGCCCC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Hypoxanthine" (Hyp) also 6-Oxypurine is a purine derivative. In certain embodiments, a hypoxanthine (Hyp) may be used in place of a guanine (G) nucleobase to break up a series of 4 or more guanosines in a row ("G-quartet"). Hypoxanthine is a modified nucleobase.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. In certain embodiments, the C9ORF72 associated disease is a C9ORF72 hexanucleotide repeat expansion associated disease. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting expression of a C9ORF72 antisense transcript" means reducing the level or expression of a C9ORF72 antisense transcript and/or its expression products (e.g., RAN translation products). In certain embodiments, C9ORF72 antisense transcripts are inhibited in the presence of an antisense compound targeting a C9ORF72 antisense transcript, including an antisense oligonucleotide targeting a C9ORF72 antisense transcript, as compared to expression of C9ORF72 antisense transcript levels in the absence of a C9ORF72 antisense compound, such as an antisense oligonucleotide.

"Inhibiting expression of a C9ORF72 sense transcript" means reducing the level or expression of a C9ORF72 sense transcript and/or its expression products (e.g., a C9ORF72 mRNA and/or protein). In certain embodiments, C9ORF72 sense transcripts are inhibited in the presence of an antisense compound targeting a C9ORF72 sense transcript, including an antisense oligonucleotide targeting a C9ORF72 sense transcript, as compared to expression of C9ORF72 sense transcript levels in the absence of a C9ORF72 antisense compound, such as an antisense oligonucleotide.

"Inhibiting the expression or activity" refers to a reduction or blockade of the expression or activity and does not necessarily indicate a total elimination of expression or activity.

"Inosine" (I) or 9-β-D-Ribosylhypoxanthine means a nucleoside that contains a hypoxanthine nucleobase.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

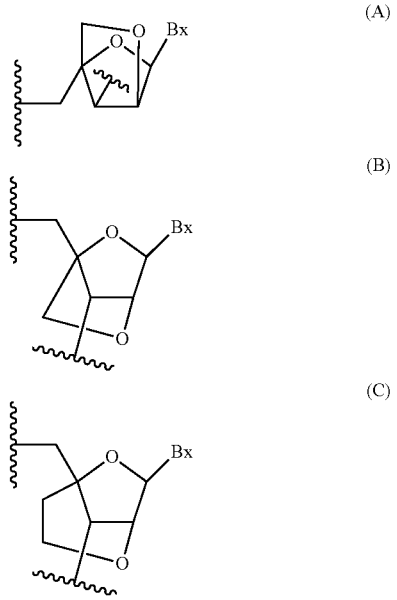

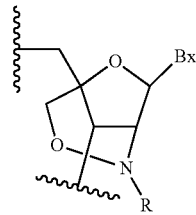

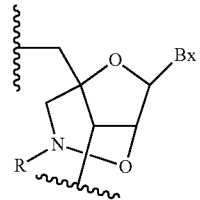

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'-bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicyclic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. Hypoxanthine (Hyp) is a modified nucleobase. An "unmodified nucleobase" means the purine bases adenine (A) and guanine (G); the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleoside in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). Hypoxanthine (Hyp) binds with adenine, thymine, or cytosine with a preference for binding with cytosine. In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. In certain embodiments, an antisense oligonucleotide targeted to C9ORF72 sense transcript is a pharmaceutical agent. In certain embodiments, an antisense oligonucleotide targeted to C9ORF72 antisense transcript is a pharmaceutical agent.

"Pharmaceutical composition" means a mixture of substances suitable for administering to as subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid.

In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form within the body or cells thereof by the action of endogenous enzymes or other chemicals or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment.

"3' target site" refers to the 3'-most nucleotide of a target segment.

"Therapeutically effective amount" means an amount of a pharmaceutical agent that provides a therapeutic benefit to an individual.

"Treat" or "treating" or "treatment" means administering a composition to effect an alteration or improvement of a disease or condition.

"Unmodified nucleobases" means the purine bases adenine (A) and guanine (G), and the pyrimidine bases (T), cytosine (C), and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Provided herein are compounds comprising a C9ORF72 antisense transcript specific inhibitor.

In certain embodiments, the C9ORF72 antisense transcript specific inhibitor is an antisense compound.

In certain embodiments, the C9ORF72 antisense transcript specific antisense compound is an antisense oligonucleotide.

In certain embodiments, the antisense oligonucleotide consists of 12-30 linked nucleosides.

In certain embodiments, the antisense oligonucleotide consists of 16-25 linked nucleosides.

In certain embodiments, the antisense oligonucleotide consists of 18-22 linked nucleosides. In certain embodiments, the antisense oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

In certain embodiments, the antisense oligonucleotide has a nucleobase sequence that is at least 90% complementary to a C9ORF72 antisense transcript.

In certain embodiments, the antisense oligonucleotide has a nucleobase sequence that is at least 95% complementary to a C9ORF72 antisense transcript.

In certain embodiments, the antisense oligonucleotide has a nucleobase sequence that is 100% complementary to a C9ORF72 antisense transcript.

In certain embodiments, the C9ORF72 antisense transcript has the nucleobase sequence of SEQ ID NO: 13.

In certain embodiments, the antisense oligonucleotide has a nucleobase sequence comprising at least 8, at least 9, at least 10, at least 11, at least 12, at least 13, at least 14, at least 15, at least 16, at least 17, at least 18, at least 19, or 20 contiguous nucleobases of a sequence selected from among SEQ ID NO: 30-84.

In certain embodiments, the antisense oligonucleotide is a modified antisense oligonucleotide.

In certain embodiments, the modified antisense oligonucleotide comprises at least one modified internucleoside linkage.

In certain embodiments, each modified internucleoside linkage is a phosphorothioate internucleoside linkage.

In certain embodiments, the at least one modified internucleoside linkage is a phosphorothioate internucleoside linkage.

In certain embodiments, the modified antisense oligonucleotide comprises at least one phosphodiester internucleoside linkage.

In certain embodiments, at least one modified nucleobase is a hypoxanthine.

In certain embodiments, at least one nucleoside of the modified antisense oligonucleotide is an inosine.

In certain embodiments, the at least one nucleoside of the modified antisense oligonucleotide comprises a modified nucleobase.

In certain embodiments, at least one modified nucleobase is a 5-methylcytosine.

In certain embodiments, the at least one nucleoside of the modified antisense oligonucleotide comprises a modified sugar.

In certain embodiments, the at least one modified sugar is a bicyclic sugar.

In certain embodiments, the bicyclic sugar comprises a chemical bridge between the 2' and 4' position of the sugar, wherein the chemical bridge is selected from: 4'-CH$_2$—O-2'; 4'-CH(CH$_3$)—O-2'; 4'-(CH$_2$)$_2$—O-2'; and 4'-CH$_2$—N(R)—O-2' wherein R is, independently, H, C$_1$-C$_{12}$ alkyl, or a protecting group.

In certain embodiments, the at least one modified sugar comprises a 2'-O-methoxyethyl group.

In certain embodiments, the antisense oligonucleotide is a gapmer.

In certain embodiments, the compound comprises at least one conjugate.

In certain embodiments, the C9ORF72 antisense transcript specific antisense compound consists of an antisense oligonucleotide.

Provided herein are pharmaceutical compositions comprising any compound described herein and a pharmaceutically acceptable diluent or carrier.

Provided herein are pharmaceutical compositions comprising a C9ORF72 antisense transcript specific inhibitor.

Provided herein are pharmaceutical compositions comprising a C9ORF72 antisense transcript specific inhibitor and a C9ORF sense transcript specific inhibitor.

In certain embodiments, the C9ORF72 sense transcript specific inhibitor is a C9ORF72 sense transcript specific antisense compound.

In certain embodiments, the C9ORF72 antisense transcript specific inhibitor is a C9ORF72 antisense transcript specific antisense compound.

In certain embodiments, the C9ORF72 sense transcript specific antisense compound is an antisense oligonucleotide.

In certain embodiments, the C9ORF72 antisense transcript specific antisense compound is an antisense oligonucleotide.

In certain embodiments, the C9ORF72 antisense transcript has the nucleobase sequence of SEQ ID NO: 13.

In certain embodiments, the C9ORF72 sense transcript has the nucleobase sequence of SEQ ID NO: 1-10.

Provided herein are uses of any compound described herein for the manufacture of a medicament for treating a neurodegenerative disease.

Provided herein are methods, comprising contacting a cell with an antisense oligonucleotide having a nucleobase sequence of any of SEQ ID NOs: 30-84.

Provided herein are methods, comprising contacting a cell with a C9ORF72 antisense transcript specific inhibitor.

Provided herein are methods, comprising contacting a cell with a C9ORF72 antisense transcript specific inhibitor and a C9ORF72 sense transcript specific inhibitor.

Provided herein are methods, comprising contacting a cell with a C9ORF72 antisense transcript specific inhibitor; and thereby reducing the level or expression of C9ORF72 antisense transcript in the cell.

Provided herein are methods, comprising contacting a cell with a C9ORF72 antisense transcript specific inhibitor and a C9ORF72 sense transcript specific inhibitor; and thereby reducing the level or expression of both C9ORF72 antisense transcript and C9ORF72 sense transcript in the cell.

In certain embodiments, the C9ORF72 antisense specific inhibitor is an antisense compound.

In certain embodiments, the C9ORF72 antisense transcript specific inhibitor is an antisense compound.

In certain embodiments, the cell is in vitro.

In certain embodiments, the cell is in an animal.

Provided herein are methods, comprising administering to an animal in need thereof a therapeutically effective amount of a C9ORF72 antisense transcript specific inhibitor.

In certain embodiments the amount is effective to reduce the level or expression of the C9ORF72 antisense transcript.

Provided herein are methods, comprising co-administering to an animal in need thereof a therapeutically effective amount of a C9ORF72 antisense transcript inhibitor and a therapeutically effective amount of a C9ORF72 sense transcript inhibitor.

In certain embodiments the therapeutically effective amount is effective to reduce the level or expression of the C9ORF72 antisense transcript and the C9ORF72 sense transcript.

In certain embodiments, wherein the C9ORF72 antisense transcript inhibitor is a C9ORF72 antisense transcript specific antisense compound.

In certain embodiments, the C9ORF72 sense transcript inhibitor is a C9ORF72 sense transcript specific antisense compound.

Provided herein are methods, comprising:
identifying an animal having a C9ORF72 associated disease; and
administering to the animal a therapeutically effective amount of a C9ORF72 antisense transcript specific inhibitor.

In certain embodiments the amount is effective to reduce the level or expression of the C9OR72 antisense transcript.

Provided herein are methods, comprising:
identifying an animal having a C9ORF72 associated disease; and
coadministering to the animal a therapeutically effective amount of a C9ORF72 antisense transcript specific inhibitor and a therapeutically effective amount of a C9ORF72 sense transcript inhibitor.

In certain embodiments the amount is effective to reduce the level or expression of the C9ORF72 antisense transcript and the C9ORF72 sense transcript.

In certain embodiments the C9ORF72 antisense transcript specific inhibitor is a C9ORF72 antisense transcript specific antisense compound.

In certain embodiments the C9ORF72 sense transcript inhibitor is a C9ORF72 sense transcript specific antisense compound.

In certain embodiments the C9ORF72 antisense transcript specific antisense compound is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

In certain embodiments the C9ORF72 sense transcript specific antisense compound is at least 80%, at least 85%, at least 90%, at least 91%, at least 92%, at least 93%, at least 94%, at least 95%, at least 96%, at least 97%, at least 98%, at least 99%, or 100% complementary to a C9ORF72 sense transcript.

In certain embodiments the C9ORF72 antisense transcript is SEQ ID NO: 13.

In certain embodiments the C9ORF72 sense transcript is any of SEQ ID NO: 1-10.

In certain embodiments the C9ORF72 associated disease is a C9ORF72 hexanucleotide repeat expansion associated disease.

In certain embodiments the C9ORF72 associated disease or C9ORF72 hexanucleotide repeat expansion associated disease is amyotrophic lateral sclerosis (ALS), frontotemporal dementia (FTD), corticobasal degeneration syndrome (CBD), atypical Parkinsonian syndrome, and olivopontocerebellar degeneration (OPCD).

In certain embodiments the amyotrophic lateral sclerosis (ALS) is familial ALS or sporadic ALS.

In certain embodiments the contacting or administering reduces C9ORF72 antisense transcript associated RAN translation products.

In certain embodiments the C9ORF72 antisense transcript associated RAN translation products are any of poly-(proline-alanine), poly-(proline-arginine), and poly-(proline-glycine).

In certain embodiments the administering and coadministering is parenteral administration.

In certain embodiments the parental administration is any of injection or infusion.

In certain embodiments the parenteral administration is any of intrathecal administration or intracerebroventricular administration.

In certain embodiments at least one symptom of a C9ORF72 associated disease or a C9ORF72 hexanucleotide repeat expansion associated disease is slowed, ameliorated, or prevented.

In certain embodiments the at least one symptom is any of motor function, respiration, muscle weakness, fasciculation and cramping of muscles, difficulty in projecting the voice, shortness of breath, difficulty in breathing and swallowing, inappropriate social behavior, lack of empathy, distractibility, changes in food preferences, agitation, blunted emotions, neglect of personal hygiene, repetitive or compulsive behavior, and decreased energy and motivation.

In certain embodiments the C9ORF72 antisense transcript specific antisense compound is an antisense oligonucleotide.

In certain embodiments the C9ORF72 sense transcript specific antisense compound is an antisense oligonucleotide.

In certain embodiments the antisense oligonucleotide is a modified antisense oligonucleotide.

In certain embodiments at least one internucleoside linkage of the antisense oligonucleotide is a modified internucleoside linkage.

In certain embodiments at least one modified internucleoside linkage is a phosphorothioate internucleoside linkage.

In certain embodiments each modified internucleoside linkage is a phosphorothioate internucleoside linkage.

In certain embodiments at least one nucleoside of the modified antisense oligonucleotide comprises a modified nucleobase.

In certain embodiments the modified nucleobase is a 5-methylcytosine.

In certain embodiments at least one nucleoside of the modified antisense oligonucleotide comprises a modified sugar.

In certain embodiments at least one modified sugar is a bicyclic sugar.

In certain embodiments the bicyclic sugar comprises a chemical bridge between the 2' and 4' position of the sugar, wherein the chemical bridge is selected from: 4'-CH$_2$—O-2'; 4'-CH(CH$_3$)—O-2'; 4'-(CH$_2$)$_2$—O-2'; and 4'-CH$_2$—N(R)—O-2' wherein R is, independently, H, C$_1$-C$_{12}$ alkyl, or a protecting group.

In certain embodiments at least one modified sugar comprises a 2'-O-methoxyethyl group.

In certain embodiments the antisense oligonucleotide is a gapmer.

The present disclosure provides the following non-limiting numbered embodiments:

Embodiment 1

A compound comprising a modified oligonucleotide consisting of 12-30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobases sequences of SEQ ID NOs: 30-99.

Embodiment 2

The compound of embodiment 1, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

Embodiment 3

The compound of embodiment 2, wherein the C9ORF72 antisense transcript has the nucleobase sequence of SEQ ID NO: 13.

Embodiment 4

The compound of any of embodiments 1-3, wherein the modified oligonucleotide is a single-stranded modified oligonucleotide.

Embodiment 5

The compound of any of embodiments 1-4, wherein the modified oligonucleotide comprises at least one modified internucleoside linkage.

Embodiment 6

The compound of any of embodiment 5, wherein the at least one modified internucleoside linkage is a phosphorothioate internucleoside linkage.

Embodiment 7

The compound of embodiments 5 or 6, wherein the modified oligonucleotide comprises at least one phosphodiester linkage.

Embodiment 8

The compound of embodiment 6, wherein each internucleoside linkage is a phosphorothioate internucleoside linkage.

Embodiment 9

The compound of any of embodiments 1-8, wherein at least one nucleoside of the modified oligonucleotide comprises a modified nucleobase.

Embodiment 10

The compound of embodiment 9, wherein the modified nucleobase is a 5-methylcytosine.

Embodiment 11

The compound of any of embodiments 1-10, wherein at least one nucleoside of the modified oligonucleotide comprises a modified sugar.

Embodiment 12

The compound of embodiment 11, wherein each nucleoside of the modified oligonucleotide comprises a modified sugar.

Embodiment 13

The compound of embodiments 11 or 12, wherein the modified sugar is a bicyclic sugar.

Embodiment 14

The compound of embodiment 13, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein R is independently selected from H, C$_1$-C$_6$ alkyl, and C$_1$-C$_6$ alkoxy.

Embodiment 15

The compound of embodiment 14, wherein the chemical bridge is 4'-CH(R)-0-2' and wherein R is methyl.

Embodiment 16

The compound of embodiment 14, wherein the chemical bridge is 4'-CH(R)-0-2' and wherein R is H.

Embodiment 17

The compound of embodiment 14, wherein the chemical bridge is 4'-CH(R)-0-2' and wherein R is —CH$_2$—O—CH$_3$.

Embodiment 18

The compound of embodiments 11 or 12, wherein the modified sugar comprises a 2'-O-methoxyethyl group.

Embodiment 19

The compound of any of embodiments 1-11 and 13-18, wherein the modified oligonucleotide is a gapmer.

Embodiment 20

The compound of embodiment 19, wherein the gapmer is selected from a 5-10-5 MOE gapmer, a 5-8-5 MOE gapmer, or a 4-8-4 MOE gapmer.

Embodiment 21

A pharmaceutical composition comprising the compound of any preceding embodiment or salt thereof and at least one of a pharmaceutically acceptable carrier or diluent.

Embodiment 22

The pharmaceutical composition of embodiment 21 further comprising a C9ORF72 sense transcript specific inhibitor.

Embodiment 23

The pharmaceutical composition of embodiment 22, wherein the C9ORF72 sense transcript specific inhibitor is any of a nucleic acid, aptamer, antibody, peptide, or small molecule.

Embodiment 24

The pharmaceutical composition of embodiment 23, wherein the nucleic acid is a single-stranded nucleic acids or a double-stranded nucleic acid.

Embodiment 25

The pharmaceutical composition of embodiment 23, wherein the nucleic acid is a siRNA.

Embodiment 26

The pharmaceutical composition of embodiment 22, wherein the C9ORF72 sense transcript inhibitor is an antisense compound.

Embodiment 27

The pharmaceutical composition of embodiment 26, wherein the antisense compound is an antisense oligonucleotide.

Embodiment 28

The pharmaceutical composition of embodiment 26, wherein the antisense compound is a modified oligonucleotide.

Embodiment 29

The pharmaceutical composition of embodiment 28, wherein the modified oligonucleotide is single-stranded.

Embodiment 30

The pharmaceutical composition of embodiments 28 or 29, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 sense transcript.

Embodiment 31

The pharmaceutical composition of embodiment 30 wherein the C9ORF72 sense transcript has the nucleobase sequence of SEQ ID NO: 1-10.

Embodiment 32

Use of the compound or composition of any preceding embodiment for the manufacture of a medicament for treating a neurodegenerative disease.

Embodiment 33

A method comprising administering to an animal the compound or composition of any preceding embodiment.

Embodiment 34

The method of embodiment 33, wherein the compound prevents, treats, ameliorates, or slows progression of at least one symptom of a C9ORF72 associated disease.

Embodiment 35

The method of embodiment 34, wherein the at least one symptom is selected from among impaired motor function, difficulty with respiration, muscle weakness, fasciculation and cramping of muscles, difficulty in projecting the voice, shortness of breath, difficulty in breathing and swallowing, inappropriate social behavior, lack of empathy, distractibility, changes in food preference, agitation, blunted emotions, neglect of personal hygiene, repetitive or compulsive behavior, and decreased energy and motivation.

Embodiment 36

The method of embodiment 34, wherein the C9ORF72 associated disease is amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 37

The method of embodiment 36, wherein the amyotrophic lateral sclerosis (ALS) is familial ALS.

Embodiment 38

The method of embodiment 36, wherein the amyotrophic lateral sclerosis (ALS) is sporadic ALS.

Embodiment 39

The method of any of embodiments 33-38, wherein the administering reduces C9ORF72 antisense transcript associated RAN translation products.

Embodiment 40

The method of embodiment 39, wherein the C9ORF72 antisense transcript associated RAN translation products are any of poly-(proline-alanine), poly-(proline-arginine), and poly-(proline-glycine).

Embodiment 41

The method of any of embodiments 33-40, wherein the administering reduces C9ORF72 antisense foci.

Embodiment 42

The method of any of embodiments 33-41, wherein the administering reduces C9ORF72 sense foci.

Embodiment 43

The method of any of embodiments 33-42, wherein the administering is parenteral administration.

Embodiment 44

The method of embodiment 43, wherein the parenteral administration is any of injection or infusion.

Embodiment 45

The method of embodiment 43, wherein the parenteral administration is directly into the central nervous system (CNS).

Embodiment 46

The method of any of embodiments 43-45, wherein the parenteral administration is any of intrathecal administration or intracerebroventricular administration.

Embodiment 47

The compound of embodiment 11, wherein the modified oligonucleotide comprises sugar residues in any of the following patterns: eeedeeeeedeeeeedeeee or eeeeedeeeeedeeeeee, wherein,
  e=a 2'-O-methoxyethylribose modified sugar, and
  d=a 2'-deoxyribose sugar.

Embodiment 48

The compound of embodiment 5, wherein the modified oligonucleotide comprises internucleoside linkages in any of the following patterns: soooosssssssssssooss, sooosssssss-sooss, ssososssosossososs, or ssssosossosossss, wherein,
  s=a phosphorothioate linkage, and
  o=a phosphodiester linkage.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)_n$—O-2' bridge, where n=1 or n=2 and 4'-$CH_2$—O—$CH_2$-2'). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y—Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-$(CH_2)_n$-O-2' bridge, wherein n is 1 or 2; and 4'-$CH_2$—O—$CH_2$-2'. In certain embodiments, the bicyclic sugar is comprises a 4'-$CH(CH_3)$—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

Nucleotide sequences that encode the C9ORF72 antisense transcript include, without limitation, the following: SEQ ID NO: 13. The sequence of SEQ ID NO: 13 is complementary to nucleotides 1159 to 1929 of SEQ ID NO: 2 (the complement of GENBANK Accession No. NT_008413.18 truncated from nucleotides 27535000 to 27565000) except that SEQ ID NO: 13 has two more hexanucleotide repeats than SEQ ID NO: 2. The sequence of the hexanucleotide repeat is GGCCCC in SEQ ID NO: 13 and GGGGCC in SEQ ID NO: 2. Thus, SEQ ID NO: 13 is 12 nucleotides longer than nucleotides 1159 to 1929 of SEQ ID NO: 2, to which it is complementary.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage. In certain embodiments, the antisense compounds targeted to a C9ORF72 nucleic acid comprise at least one phosphodiester linkage and at least one phosphorothioate linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_1)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U.S.A*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; and PCT International Applications Nos.: PCT/US2008/068922; PCT/US2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$-, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiment, bicyclic nucleosides have the formula:

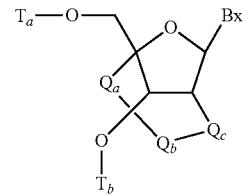

wherein:

Bx is a heterocyclic base moiety;

-Q$_a$-Q$_b$-Q$_c$- is —CH$_2$—N(R$^c$)—CH$_2$—, —C(=O)—N(R$^c$)—CH$_2$—, —CH$_2$—O—N(R$^c$)—, —CH$_2$—N(R$^c$)—O— or —N(R$^c$)—O—CH$_2$;

R$^c$ is C$_1$-C$_{12}$ alkyl or an amino protecting group; and

T$_a$ and T$_b$ are each, independently H, a hydroxyl protecting group, a conjugate group, a reactive phosphorus group, a phosphorus moiety or a covalent attachment to a support medium.

In certain embodiments, bicyclic nucleosides have the formula:

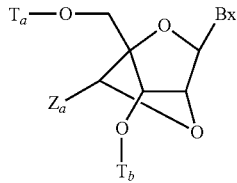

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

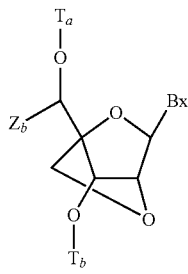

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

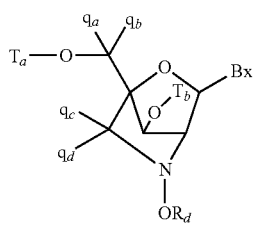

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

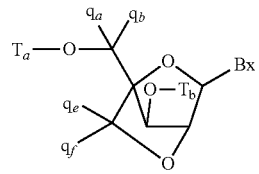

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'-$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'-$CH_2$—O-2' and 4'-$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides have the formula:

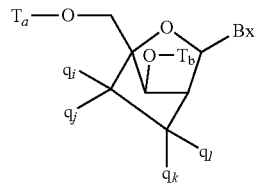

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_i$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, (F) methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) vinyl BNA as depicted below.

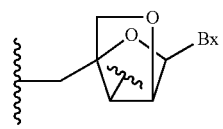
(A)

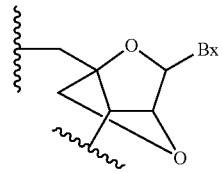
(B)

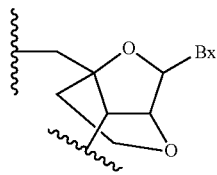
(C)

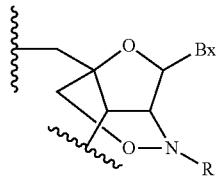
(D)

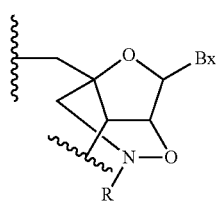
(E)

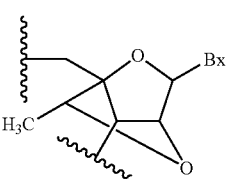
(F)

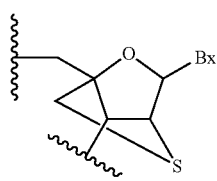
(G)

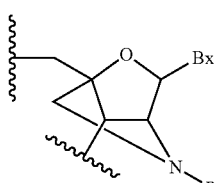
(H)

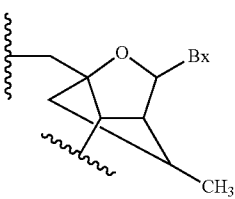
(I)

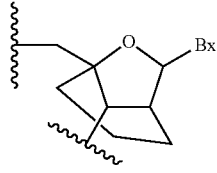
(J)

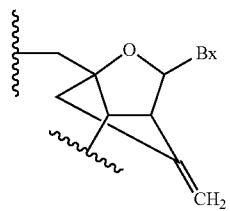

(K)

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), mannitol nucleic acid (MNA) (see Leumann, Bioorg. Med. Chem., 2002, 10, 841-854) or fluoro HNA (F-HNA) having a tetrahydropyranyl ring system as illustrated below.

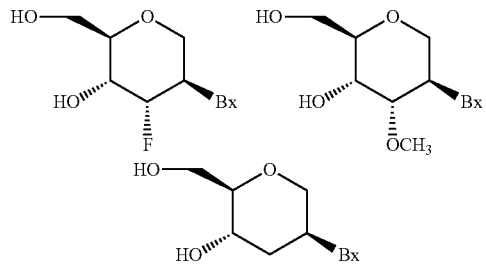

In certain embodiment, sugar surrogates are selected having the formula:

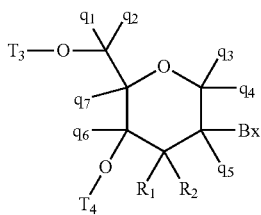

wherein:
Bx is a heterocyclic base moiety;
$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and
one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166, 315; 5,185,444; and 5,034,506). As used here, the term "morpholino" means a sugar surrogate having the following formula:

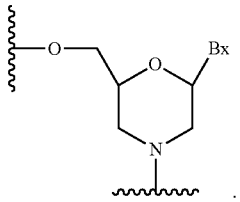

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$-O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., J. Am. Chem. Soc., 2008, 130(6), 1979-1984; Horváth et al., Tetrahedron Letters, 2007, 48, 3621-3623; Nauwelaerts et al., J. Am. Chem. Soc., 2007, 129(30), 9340-9348; Gu et al., Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J. Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

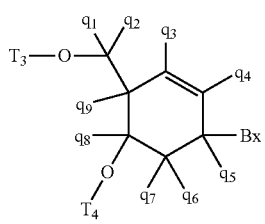

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. *Bioorg. & Med. Chem.*, 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N($R_m$)($R_n$), or O—$CH_2$—C($=$O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$", "2'-O-methyl" or "2'-methoxy" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH(CH₃)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900

Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Strand Specific Semi-Quantitative PCR Analysis of Target RNA Levels

Analysis of specific, low abundance target RNA strand levels may be accomplished by reverse transcription, PCR, and gel densitometry analysis using the Gel Logic 200 Imaging System and Kodak MI software (Kodak Scientific Imaging Systems, Rochester, N.Y., USA) according to manufacturer's instructions.

RT-PCR reactions are carried out as taught in Ladd, P. D., et al, (Human Molecular Genetics, 2007, 16, 3174-3187) and in Sopher, B. L., et al, (Neuron, 2011, 70, 1071-1084) and such methods are well known in the art.

The PCR amplification products are loaded onto gels, stained with ethidium bromide, and subjected to densitometry analysis. Mean intensities from regions of interest (ROI) that correspond to the bands of interest in the gel are measured.

Gene (or RNA) target quantities obtained by PCR are normalized using the expression level of a housekeeping gene whose expression is constant, such as GAPDH. Expression of the housekeeping gene (or RNA) is analyzed and measured using the same methods as the target.

Probes and primers are designed to hybridize to a C9ORF72 nucleic acid. Methods for designing RT-PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid derived from either DNA strand. For example, antisense oligonucleotides described herein may hybridize to a C9ORF72 antisense transcript or a C9ORF72 sense transcript. Antisense oligonucleotides described herein may hybridize to a C9ORF72 nucleic acid in any stage of RNA processing. Described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 1, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72 derived from the sense strand. In certain embodiments, the antisense oligonucleotides described herein selectively hybridize to certain variants of C9ORF72 derived from the sense strand. In certain embodiments, the antisense oligonucleotides described herein selectively hybridize to variants of C9ORF72 derived from the sense strand containing a hexanucleotide repeat expansion. In certain embodiments, the antisense oligonucleotides described herein selectively hybridize to pre-mRNA variants containing a hexanucleotide repeat. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG.

In certain embodiments, the antisense oligonucleotides described herein inhibit expression of all variants of C9ORF72 derived from the sense strand. In certain embodiments, the antisense oligonucleotides described herein inhibit expression of all variants of C9ORF72 derived from the sense strand equally. In certain embodiments, the antisense oligonucleotides described herein preferentially inhibit expression of one or more variants of C9ORF72 derived from the sense strand. In certain embodiments, the antisense oligonucleotides described herein preferentially inhibit expression of variants of C9ORF72 derived from the sense strand containing a hexanucleotide repeat expansion. In certain embodiments, the antisense oligonucleotides described herein selectively inhibit expression of pre-mRNA variants containing the hexanucleotide repeat. In certain embodiments, the antisense oligonucleotides described herein selectively inhibit expression of C9ORF72 pathogenic associated mRNA variants. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG. In certain embodiments, the hexanucleotide repeat expansion forms C9ORF72 sense foci. In certain embodiments, antisense oligonucleotides described herein are useful for reducing C9ORF72 sense foci. C9ORF72 sense foci may be reduced in terms of percent of cells with foci as well as number of foci per cell.

C9OFF72 Features

Antisense oligonucleotides described herein may hybridize to any C9ORF72 nucleic acid at any state of processing within any element of the C9ORF72 gene. In certain embodiments, antisense oligonucleotides described herein may target the antisense transcript, e.g., SEQ ID NO: 13. In certain embodiments, antisense oligonucleotides described herein may hybridize to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 described below. Antisense oligonucleotides described herein may also target nucleic acids not characterized below and such nucleic acid may be characterized in GENBANK. Moreover, antisense oligonucleotides described herein may also target elements other than exons and such elements as characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
|---|---|---|---|---|
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 1E | 1 | 35 | 1135 | 1169 |
| exon 2 | 36 | 524 | 7839 | 8326 |

TABLE 4-continued

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
|---|---|---|---|---|
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, administration of an antisense compound targeted to a C9ORF72 antisense transcript results in reduction of C9ORF72 antisense transcript expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 antisense transcript results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values. In certain embodiments, administration of a C9ORF72 antisense compound reduces the number of cells with C9ORF72 antisense foci and/or the number of C9ORF72 antisense foci per cell.

In certain embodiments, administration of an antisense compound targeted to a C9ORF72 sense transcript results in reduction of a C9ORF72 sense transcript expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 sense transcript results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values. In certain embodiments, administration of a C9ORF72 antisense compound reduces the number of cells with C9ORF72 sense foci and/or the number of C9ORF72 sense foci per cell.

In certain embodiments, pharmaceutical compositions comprising an antisense compound targeted to a C9ORF72 nucleic are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 antisense transcript specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Certain Human Therapeutics

The human C9ORF72 antisense transcript specific antisense compounds described herein are being evaluated as possible human therapeutics. Various parameters of potency, efficacy, and/or tolerability are being examined. Such parameters include in vitro inhibition of C9ORF72 antisense transcript; in vitro dose response (IC50); in vivo inhibition of C9ORF72 antisense transcript in a transgenic animal containing a human C9ORF72 transgene in relevant tissues (e.g., brain and/or spinal cord); and/or tolerability in mouse, rat, dog, and/or primate. Tolerability markers that may be measured include blood and serum chemistry parameters, CSF chemistry parameters, body and organ weights, general observations and/or behavioral tests, and/or biochemical markers such as GFAP and/or AIF1. Acute or long term tolerability may be measured.

Certain Assays for Measuring C9ORF72 Antisense Transcripts

Certain assays described herein are directed to the reduction of C9ORF72 antisense transcript. Additional assays may be used to measure the reduction of C9ORF72 antisense transcript. Additional controls may be used as a baseline for measuring the reduction of C9ORF72 transcript.

Certain Hotspot Regions
1. Nucleobases 196-280 of SEQ ID NO: 13

In certain embodiments, antisense oligonucleotides are designed to target nucleobases 196-280 of SEQ ID NO: 13. In certain embodiments, nucleobases 196-280 are a hotspot region. In certain embodiments, nucleobases 196-280 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers.

In certain embodiments, nucleobases 196-280 are targeted by the following ISIS numbers: 687280, 687281, 687282, 687283, 687284, 687285, 687286, 687287, 687288, 687289, 687290, 687291, 687292, and 687293.

In certain embodiments, nucleobases 196-280 are targeted by the following SEQ ID NOs: 69, 70, 71, 72, 73, 74, 75, 76, 77, 78, 79, 80, 81, and 82.

In certain embodiments, antisense oligonucleotides targeting nucleobases 196-280 achieve at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, or at least 73% reduction of C9ORF72 antisense transcript in vitro.

2. Nucleobases 286-315 of SEQ ID NO: 13

In certain embodiments, antisense oligonucleotides are designed to target nucleobases 286-315 of SEQ ID NO: 13. In certain embodiments, nucleobases 286-315 are a hotspot region. In certain embodiments, nucleobases 286-315 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers.

In certain embodiments, nucleobases 286-315 are targeted by the following ISIS numbers: 687277, 687278, and 687279.

In certain embodiments, nucleobases 286-315 are targeted by the following SEQ ID NOs: 66, 67, and 68.

In certain embodiments, antisense oligonucleotides targeting nucleobases 286-315 achieve at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, or at least 64% reduction of C9ORF72 antisense transcript in vitro.

3. Nucleobases 321-415 of SEQ ID NO: 13

In certain embodiments, antisense oligonucleotides are designed to target nucleobases 321-415 of SEQ ID NO: 13. In certain embodiments, nucleobases 321-415 are a hotspot region. In certain embodiments, nucleobases 321-415 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers.

In certain embodiments, nucleobases 321-415 are targeted by the following ISIS numbers: 687261, 687262, 687263, 687264, 687265, 687266, 687267, 687268, 687269, 687270, 687271, 687272, 687273, 687274, 687275, and 687276.

In certain embodiments, nucleobases 321-415 are targeted by the following SEQ ID NOs: 50, 51, 52, 53, 54, 55, 56, 57, 58, 59, 60, 61, 62, 63, 64, 65.

In certain embodiments, antisense oligonucleotides targeting nucleobases 321-415 achieve at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, or at least 70% reduction of C9ORF72 antisense transcript in vitro.

4. Nucleobases 451-516 of SEQ ID NO: 13

In certain embodiments, antisense oligonucleotides are designed to target nucleobases 451-516 of SEQ ID NO: 13. In certain embodiments, nucleobases 451-516 are a hotspot region. In certain embodiments, nucleobases 451-516 are targeted by antisense oligonucleotides. In certain embodiments, the antisense oligonucleotides are 16, 18, or 20 nucleobases in length. In certain embodiments, the antisense oligonucleotides are gapmers. In certain embodiments, the gapmers are 5-10-5 MOE gapmers, 5-8-5 MOE gapmers, 4-8-4 MOE gapmers. In certain embodiments, each nucleoside of the antisense oligonucleotides is modified with a 2'-MOE substitution. In certain embodiments, the antisense oligonucleotides contain one or more inosine residues.

In certain embodiments, nucleobases 451-516 are targeted by the following ISIS numbers: 687255, 687256, 687257, 687258, 687259, 687260, 730389, 730390, 730391, 730392, 730393, 730394, 730395, 730396, 730397, 730398, 730399, 730400, 730401, 730402, 730403, 730404, 730405, 730406, 730407, 730408, 730409, 730410, 730411, 730412, 737821, 742033, 742034, and 742035.

In certain embodiments, nucleobases 451-516 are targeted by the following SEQ ID NOs: 44, 45, 46, 47, 48, 49, 83, 84, 85, 86, 87, 88, 89, 90, 91, 92, 93, 94, 95, 96, 98, and 99.

In certain embodiments, antisense oligonucleotides targeting nucleobases 451-516 achieve at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, or at least 78% reduction of C9ORF72 antisense transcript in vitro.

5. Nucleobases 527-588 of SEQ ID NO: 13

In certain embodiments, antisense oligonucleotides are designed to target nucleobases 527-588 of SEQ ID NO: 13. In certain embodiments, nucleobases 527-588 are a hotspot region. In certain embodiments, nucleobases 527-588 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers.

In certain embodiments, nucleobases 527-588 are targeted by the following ISIS numbers: 687247, 687248, 687249, 687250, 687251, 687252, 687253, and 687254.

In certain embodiments, nucleobases 527-588 are targeted by the following SEQ ID NOs: 36, 37, 38, 39, 40, 41, 42, and 43.

In certain embodiments, antisense oligonucleotides targeting nucleobases 527-588 achieve at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, or at least 73% reduction of C9ORF72 antisense transcript in vitro.

6. Nucleobases 608-636 of SEQ ID NO: 13

In certain embodiments, antisense oligonucleotides are designed to target nucleobases 608-636 of SEQ ID NO: 13. In certain embodiments, nucleobases 608-636 are a hotspot region. In certain embodiments, nucleobases 608-636 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers.

In certain embodiments, nucleobases 608-636 are targeted by the following ISIS numbers: 687243, 687244, 687245, and 687246.

In certain embodiments, nucleobases 608-636 are targeted by the following SEQ ID NOs: 32, 33, 34, and 35.

In certain embodiments, antisense oligonucleotides targeting nucleobases 608-636 achieve at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, or at least 72% reduction of C9ORF72 antisense transcript in vitro.

7. Nucleobases 704-726 of SEQ ID NO: 13

In certain embodiments, antisense oligonucleotides are designed to target nucleobases 704-726 of SEQ ID NO: 13. In certain embodiments, nucleobases 704-726 are a hotspot region. In certain embodiments, nucleobases 704-726 are targeted by antisense oligonucleotides. In certain embodiments, the antisense oligonucleotides are 20 nucleobases in length. In certain embodiments, the antisense oligonucleotides are gapmers. In certain embodiments, the gapmers are 5-10-5 MOE gapmers.

In certain embodiments, nucleobases 704-726 are targeted by the following ISIS numbers: 687241 and 687242.

In certain embodiments, nucleobases 704-726 are targeted by the following SEQ ID NOs: 30 and 31.

In certain embodiments, antisense oligonucleotides targeting nucleobases 704-726 achieve at least 19%, at least 20%, or at least 21% reduction of C9ORF72 antisense transcript in vitro.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of C9ORF72 Antisense Transcript with Oligonucleotides Antisense oligonucleotides (ASOs) targeting the human C9ORF72 antisense transcript were made and tested for inhibition of target transcript expression in vitro. All of the ASOs in the table below except Isis Numbers 742033 and 742035 are 5-10-5 MOE gapmers with phosphorothioate internucleoside linkages throughout the gapmers. They are 20 nucleosides in length, with a central gap segment consisting of ten 2'-deoxynucleosides that is flanked by wing segments in the 5' direction and the 3' direction consisting of five nucleosides each. Each nucleoside in the 5' and 3' wing segments has a 2'-MOE modification. All cytosine residues throughout each gapmer are 5-methylcytosines. Isis No. 742033 is a 5-10-5 MOE gapmer with phosphodiester ("o") and phosphorothioate ("s") internucleoside linkages arranged in order from 5' to 3': soooosssssssssssooss. Isis No. 742035 is a 5-8-5 MOE gapmer with a central gap segment consisting of eight 2'-deoxynucleosides and internucleoside linkages arranged in order from 5' to 3': sooosssssssssooss. All cytosine residues in Isis Numbers 742033 and 742035 are 5-methylcytosines.

Isis Numbers 742033 and 742035 also contain inosine residues, indicated by "I". In the table below, "Start" indicates the 5'-most nucleoside to which the gapmer is targeted in the target transcript sequence. "Stop" indicates the 3'-most nucleoside to which the gapmer is targeted in the target transcript sequence. Each gapmer listed in the table below is targeted to a putative antisense transcript sequence, designated herein as SEQ ID NO: 13. The sequence of SEQ ID NO: 13 is complementary to nucleotides 1159 to 1929 of SEQ ID NO: 2 (the complement of GENBANK Accession No. NT_008413.18 truncated from nucleotides 27535000 to 27565000) except that SEQ ID NO: 13 has two more hexanucleotide repeats than SEQ ID NO: 2. The sequence of the hexanucleotide repeat is GGCCCC in SEQ ID NO: 13 and GGGGCC in SEQ ID NO: 2. Thus, SEQ ID NO: 13 is 12 nucleotides longer than nucleotides 1159 to 1929 of SEQ ID NO: 2, to which it is complementary. Isis No. 129700 is a negative control ASO that does not target the C9ORF72 antisense transcript.

bEND cells were cultured in 24 well plates at 45,000-50,000 cells/well 24 hours before the first of two transfections. The cells were first transfected with 0.2 µg/well of a plasmid expressing the C9ORF72 antisense transcript (SEQ ID NO: 13) and 0.5 µL Lipofectamine 2000 (Life Technologies, Carlsbad, Calif.) in OptiMEM medium. Four to six hours later, the media was replaced. 24 hours after the first transfection (18-20 hours after media replacement), the bEND cells were transfected with 25 nM of an ASO listed in the table below and 0.5 µL Lipofectamine 2000 in OptiMEM medium or with no ASO. Just prior to transfection, ASOs comprising a GGGGCC repeat with or without guanosine to inosine substitutions (Isis Numbers 687258, 687259, 687260, 742033, and 742035) were heated at 90° C. for five minutes, then placed on ice briefly before dilution in OptiMEM. Total RNA was isolated from the cells 24 hours after the second transfection using TRIzol (Life Technologies) according to the manufacturer's directions. Two DNase reactions were performed, one on the column during RNA purification, and one after purification using TURBO DNase (Life Technologies).

Strand specific RT-qPCR was performed on the isolated RNA to generate and amplify C9ORF72 antisense cDNA using one or two of three different primer sets, LTS01222, LTS01221, and C9ATS3'-1. The LTS01222 sequences are: RT primer: CGACTGGAGCACGAGGACACT-GAAAAGATGACGCTTGGTGTGTCA (SEQ ID NO: 14), forward PCR primer: CCCACACCTGCTCTTGCTAGA (SEQ ID NO: 15), reverse PCR primer: CGACTGGAG-CACGAGGACACTG (SEQ ID NO: 16), and probe: CCCAAAAGAGAAGCAACCGGGCA (SEQ ID NO: 17). The LTS01221 sequences are: RT primer: CGACTGGAG-CACGAGGACACTGACGGCTGCCGGGAAGA (SEQ ID NO: 18), forward PCR primer: AGAAAT-GAGAGGGAAAGTAAAAATGC (SEQ ID NO: 19), reverse PCR primer: CGACTGGAGCACGAGGACACTG (SEQ ID NO: 20), and probe: AGGAGAGCCCCCGCTTC-TACCCG (SEQ ID NO: 21). The C9ATS3'-1 sequences are: RT primer: CGACTGGAGCACGAGGACACTGACGCT-GAGGGTGAACAAGAA (SEQ ID NO: 22), forward PCR primer: GAGTTCCAGAGCTTGCTACAG (SEQ ID NO: 23), reverse PCR primer: CGACTGGAGCACGAGGA-CACTG (SEQ ID NO: 24), and probe: CTGCGGTT-GTTTCCCTCCTTGTTT (SEQ ID NO: 25). RT-qPCR was also performed on the isolated RNA using Express One-Step Superscript qRT-PCR Kit (Life Technologies, Carlsbad, Calif.) according to manufacturer's instructions to generate and amplify GAPDH cDNA, as a control, using forward PCR primer: GGCAAATTCAACGGCACAGT (SEQ ID NO: 26), reverse PCR primer: GGGTCTCGCTCCTG-GAAGAT (SEQ ID NO: 27), and probe: AAGGCCGA-GAATGGGAAGCTTGTCATC (SEQ ID NO: 28). The resulting C9ORF72 antisense levels were normalized to GAPDH. These normalized values for C9ORF72 antisense transcript expression in cells treated with an ASO were then compared to the normalized values for C9ORF72 antisense transcript expression in control cells that were transfected with the C9ORF72 antisense plasmid but not an ASO. The results for each primer probe set are shown in the table below as percent inhibition of C9ORF72 antisense transcript expression relative to the control cells that were not transfected with an ASO. A result of 0% inhibition indicates that the C9ORF72 antisense transcript levels were equal to that of control cells that were not transfected with an ASO. A negative value for % inhibition indicates that the C9ORF72 antisense transcript levels were higher than that of control cells that were not transfected with an ASO. A result of "n/a"

indicates that the corresponding primer probe set was not used to analyze the indicated sample. The results show that many ASOs inhibited human C9ORF72 antisense transcript expression. The absolute inhibition results varied across different primer probe sets, but the relative potencies of the ASOs were very similar across different primer probe sets.

TABLE 6

C9ORF72 Antisense RNA Inhibition by Antisense Oligonucleotides

| Isis No. | Start | Stop | Sequence | LTS 01222 | LTS 01221 | C9ATS3'-1 | SEQ ID No. |
|---|---|---|---|---|---|---|---|
| 129700 | n/a | n/a | TAGTGCGGACCTACCCACGA | 98 | 92 | 101 | 29 |
| 687241 | 707 | 726 | GGTGTGTCAGCCGTCCCTGC | n/a | 19 | 21 | 30 |
| 687242 | 704 | 723 | GTGTCAGCCGTCCCTGCTGC | n/a | -44 | -1 | 31 |
| 687243 | 617 | 636 | TGTTTTTCCCACCCTCTCTC | 70 | 20 | n/a | 32 |
| 687244 | 614 | 633 | TTTTCCCACCCTCTCTCCCC | 68 | 21 | n/a | 33 |
| 687245 | 611 | 630 | TCCCACCCTCTCTCCCCACT | 72 | -5 | n/a | 34 |
| 687246 | 608 | 627 | CACCCTCTCTCCCCACTACT | 59 | 17 | n/a | 35 |
| 687247 | 569 | 588 | GAGGGTGAACAAGAAAAGAC | 71 | 51 | n/a | 36 |
| 687248 | 557 | 576 | GAAAAGACCTGATAAAGATT | 50 | 30 | n/a | 37 |
| 687249 | 542 | 561 | AGATTAACCAGAAGAAAACA | 54 | 21 | n/a | 38 |
| 687250 | 539 | 558 | TTAACCAGAAGAAAACAAGG | 63 | 35 | n/a | 39 |
| 687251 | 536 | 555 | ACCAGAAGAAAACAAGGAGG | 73 | 41 | n/a | 40 |
| 687252 | 533 | 552 | AGAAGAAAACAAGGAGGGAA | 44 | 33 | n/a | 41 |
| 687253 | 530 | 549 | AGAAAACAAGGAGGGAAACA | 68 | 47 | n/a | 42 |
| 687254 | 527 | 546 | AAACAAGGAGGGAAACAACC | 57 | 33 | n/a | 43 |
| 687255 | 497 | 516 | GCAAGCTCTGGAACTCAGGA | 51 | n/a | n/a | 44 |
| 687256 | 494 | 513 | AGCTCTGGAACTCAGGAGTC | 57 | n/a | n/a | 45 |
| 687257 | 483 | 502 | TCAGGAGTCGCGCGCTAGGG | 68 | n/a | n/a | 46 |
| 687258 | 480 | 499 | GGAGTCGCGCGCTAGGGGCC | 54 | n/a | n/a | 47 |
| 687259 | 477 | 496 | GTCGCGCGCTAGGGGCCGGG | 63 | n/a | n/a | 48 |
| 687260 | 474 | 493 | GCGCGCTAGGGGCCGGGGCC | 44 | n/a | n/a | 49 |
| 687261 | 396 | 415 | GGGCTGCGGTTGCGGTGCCT | 58 | n/a | 56 | 50 |
| 687262 | 391 | 410 | GCGGTTGCGGTGCCTGCGCC | 55 | n/a | 55 | 51 |
| 687263 | 386 | 405 | TGCGGTGCCTGCGCCCGCGG | 51 | n/a | 53 | 52 |
| 687264 | 381 | 400 | TGCCTGCGCCCGCGGCGGCG | 40 | n/a | 35 | 53 |
| 687265 | 376 | 395 | GCGCCCGCGGCGGCGGAGGC | 16 | n/a | 15 | 54 |
| 687266 | 371 | 390 | CGCGGCGGCGGAGGCGCAGG | 45 | n/a | 40 | 55 |
| 687267 | 366 | 385 | CGGCGGAGGCGCAGGCGGTG | 46 | n/a | 45 | 56 |
| 687268 | 361 | 380 | GAGGCGCAGGCGGTGGCGAG | 29 | n/a | 39 | 57 |
| 687269 | 356 | 375 | GCAGGCGGTGGCGAGTGGGT | 51 | n/a | 52 | 58 |
| 687270 | 351 | 370 | CGGTGGCGAGTGGGTGAGTG | 56 | n/a | 55 | 59 |
| 687271 | 346 | 365 | GCGAGTGGGTGAGTGAGGAG | 70 | n/a | 69 | 60 |
| 687272 | 341 | 360 | TGGGTGAGTGAGGAGGCGGC | 69 | n/a | 69 | 61 |
| 687273 | 336 | 355 | GAGTGAGGAGGCGGCATCCT | 56 | n/a | 51 | 62 |
| 687274 | 331 | 350 | AGGAGGCGGCATCCTGGCGG | 49 | n/a | 46 | 63 |

TABLE 6-continued

C9ORF72 Antisense RNA Inhibition by Antisense Oligonucleotides

| Isis No. | Start | Stop | Sequence | LTS 01222 | LTS 01221 | C9ATS3'-1 | SEQ ID No. |
|---|---|---|---|---|---|---|---|
| 687275 | 326 | 345 | GCGGCATCCTGGCGGGTGGC | 54 | n/a | 51 | 64 |
| 687276 | 321 | 340 | ATCCTGGCGGGTGGCTGTTT | 66 | n/a | 64 | 65 |
| 687277 | 296 | 315 | TCGGCTGCCGGGAAGAGGCG | 62 | n/a | 64 | 66 |
| 687278 | 291 | 310 | TGCCGGGAAGAGGCGCGGGT | 46 | n/a | 41 | 67 |
| 687279 | 286 | 305 | GGAAGAGGCGCGGGTAGAAG | 6 | n/a | 8 | 68 |
| 687280 | 261 | 280 | GCTCTCCTCAGAGCTCGACG | 48 | n/a | 50 | 69 |
| 687281 | 256 | 275 | CCTCAGAGCTCGACGCATTT | 48 | n/a | 48 | 70 |
| 687282 | 251 | 270 | GAGCTCGACGCATTTTTACT | 57 | n/a | 55 | 71 |
| 687283 | 246 | 265 | CGACGCATTTTTACTTTCCC | 66 | n/a | 62 | 72 |
| 687284 | 241 | 260 | CATTTTTACTTTCCCTCTCA | 66 | n/a | 67 | 73 |
| 687285 | 236 | 255 | TTACTTTCCCTCTCATTTCT | 64 | n/a | 61 | 74 |
| 687286 | 231 | 250 | TTCCCTCTCATTTCTCTGAC | 60 | n/a | 56 | 75 |
| 687287 | 226 | 245 | TCTCATTTCTCTGACCGAAG | 64 | n/a | 45 | 76 |
| 687288 | 221 | 240 | TTTCTCTGACCGAAGCTGGG | 70 | n/a | 67 | 77 |
| 687289 | 216 | 235 | CTGACCGAAGCTGGGTGTCG | 71 | n/a | 66 | 78 |
| 687290 | 211 | 230 | CGAAGCTGGGTGTCGGGCTT | 64 | n/a | 65 | 79 |
| 687291 | 206 | 225 | CTGGGTGTCGGGCTTTCGCC | 73 | n/a | 68 | 80 |
| 687292 | 201 | 220 | TGTCGGGCTTTCGCCTCTAG | 66 | n/a | 67 | 81 |
| 687293 | 196 | 215 | GGCTTTCGCCTCTAGCGACT | 70 | n/a | 71 | 82 |
| 742033 | 456 462 | 475 481 | CCGGGICCGIGGCCIGGGCC | 74 | 36 | 50 | 83 |
| 742035 | 454 460 466 | 471 477 483 | GGCCGIGGCCGGIGCCGG | 37 | n/a | 18 | 84 |

Example 2: Dose Dependent Inhibition of C9ORF72 Antisense Transcript with an Oligonucleotide Targeting a Hexanucleotide Repeat Isis No. 742033 (see Example 1) was tested for dose dependent inhibition of C9ORF72 antisense transcript expression in vitro. bEND cells were cultured and treated as described in Example 1. During the second transfection, cells received Isis No. 742033 at a concentration listed in the table below or they received no ASO as a control. Total RNA was isolated and analyzed as described in Example 1 using primer probe set C9ATS3'-1.

TABLE 7

C9ORF72 Antisense RNA Inhibition by Isis No. 742033

| Concentration of Isis No. 742033 (nM) | % Inhibition |
|---|---|
| 3.125 | 39 |
| 6.25 | 65 |

TABLE 7-continued

C9ORF72 Antisense RNA Inhibition by Isis No. 742033

| Concentration of Isis No. 742033 (nM) | % Inhibition |
|---|---|
| 12.5 | 68 |
| 25.0 | 72 |

Example 3: Antisense Inhibition of C9ORF72 Antisense Transcript with Oligonucleotides Antisense oligonucleotides (ASOs) targeting the human C9ORF72 antisense transcript were made and tested for inhibition of C9ORF72 antisense transcript expression in vitro. ASOs 730401-730406 in the table below are 5-8-5 MOE gapmers with phosphorothioate internucleoside linkages throughout the gapmers. ASOs 730407-730412 in the table below are 4-8-4 MOE gapmers with phosphorothioate internucleoside linkages throughout the gapmers. ASOs 730401-730412 all have a central gap segment consisting of eight 2'-deoxynucleosides that is flanked by wing segments in the 5' direction and the 3' direction consisting of four or five nucleosides each. Each nucleoside in the 5' and 3' wing segments has a 2'-MOE modification. All cytosine residues throughout each gapmer are 5-methylcytosines. In the table below, "Start" indicates the 5'-most nucleoside to which the gapmer is targeted in the target transcript sequence. "Stop" indicates the 3'-most nucleoside to which the gapmer is targeted in the target transcript sequence. Each gapmer listed in the table below is targeted to a putative antisense transcript sequence, designated herein as SEQ ID NO: 13. The sequence of SEQ ID NO: 13 is complementary to nucleotides 1159 to 1929 of SEQ ID NO: 2 (the complement of GENBANK Accession No. NT_008413.18 truncated from nucleotides 27535000 to 27565000) except that SEQ ID NO: 13 has two more hexanucleotide repeats than SEQ ID NO: 2. The sequence of the hexanucleotide repeat is GGC-CCC in SEQ ID NO: 13 and GGGGCC in SEQ ID NO: 2. Thus, SEQ ID NO: 13 is 12 nucleotides longer than nucleotides 1159 to 1929 of SEQ ID NO: 2, to which it is complementary. Isis No. 129700 is a negative control ASO that does not target the C9ORF72 antisense transcript, and 742035 was included for comparison, as it was described and tested in Example 1.

bEND cells were cultured and treated as described in Example 1. Strand specific RT-qPCR was performed on the isolated RNA, as described in Example 1, using the primer sets LTS01222 and LTS01221. The resulting normalized C9ORF72 antisense levels were then compared to the normalized values for C9ORF72 antisense transcript expression in control cells that were transfected with the C9ORF72 antisense plasmid but not an ASO. The results for each primer probe set are shown in the table below as percent inhibition of C9ORF72 antisense transcript expression relative to the control cells that were not transfected with an ASO. The values in the table below are the averages of two separate experiments. A result of 0% inhibition indicates that the C9ORF72 antisense transcript levels were equal to that of control cells that were not transfected with an ASO. A negative value for % inhibition indicates that the C9ORF72 antisense transcript levels were higher than that of control cells that were not transfected with an ASO. A result of "n/a" indicates that the corresponding primer probe set was not used to analyze the indicated sample. The results show that many ASOs inhibited human C9ORF72 antisense transcript expression. The absolute inhibition results varied across different primer probe sets, but the relative potencies of the ASOs were similar across different primer probe sets.

TABLE 8

Inhibition of C9ORF72 Antisense Transcript by Antisense Oligonucleotides

| Isis No. | Start | Stop | Sequence | LTS 01222 | LTS 01221 | SEQ ID No. |
|---|---|---|---|---|---|---|
| 129700 | n/a | n/a | TAGTGCGGACCTACCCACGA | 11 | 11 | 29 |
| 730401 | 456 | 473 | GGGGCCGGGGCCGGGGCC | 71 | 38 | 85 |
|  | 462 | 479 |  |  |  |  |
|  | 468 | 485 |  |  |  |  |
| 730402 | 451 | 468 | CGGGGCCGGGGCCGGGGC | 67 | 10 | 86 |
|  | 457 | 474 |  |  |  |  |
|  | 463 | 480 |  |  |  |  |
| 730403 | 452 | 469 | CCGGGGCCGGGGCCGGGG | 64 | 21 | 87 |
|  | 458 | 475 |  |  |  |  |
|  | 464 | 481 |  |  |  |  |
| 730404 | 459 | 476 | GCCGGGGCCGGGGCCGGG | 65 | 34 | 88 |
|  | 465 | 482 |  |  |  |  |
| 730405 | 454 | 471 | GGCCGGGGCCGGGGCCGG | 49 | 22 | 89 |
|  | 460 | 477 |  |  |  |  |
|  | 466 | 483 |  |  |  |  |
| 730406 | 455 | 472 | GGGCCGGGGCCGGGGCCG | 41 | 12 | 90 |
|  | 461 | 478 |  |  |  |  |
|  | 467 | 484 |  |  |  |  |
| 730407 | 456 | 471 | GGCCGGGGCCGGGGCC | 78 | 44 | 91 |
|  | 462 | 477 |  |  |  |  |
|  | 468 | 483 |  |  |  |  |
| 730408 | 451 | 466 | GGGCCGGGGCCGGGGC | 68 | 24 | 92 |
|  | 457 | 472 |  |  |  |  |
|  | 463 | 478 |  |  |  |  |
|  | 469 | 484 |  |  |  |  |
| 730409 | 452 | 467 | GGGGCCGGGGCCGGGG | 66 | 38 | 93 |
|  | 458 | 473 |  |  |  |  |
|  | 464 | 479 |  |  |  |  |
|  | 470 | 485 |  |  |  |  |
| 730410 | 453 | 468 | CGGGGCCGGGGCCGGG | 67 | 38 | 94 |
|  | 459 | 474 |  |  |  |  |
|  | 465 | 480 |  |  |  |  |

TABLE 8-continued

Inhibition of C9ORF72 Antisense Transcript by Antisense Oligonucleotides

| Isis No. | Start | Stop | Sequence | LTS 01222 | LTS 01221 | SEQ ID No. |
|---|---|---|---|---|---|---|
| 730411 | 454 | 469 | CCGGGGCCGGGGCCGG | 63 | 16 | 95 |
|  | 460 | 475 |  |  |  |  |
|  | 466 | 481 |  |  |  |  |
| 730412 | 455 | 470 | GCCGGGGCCGGGGCCG | 73 | 38 | 96 |
|  | 461 | 476 |  |  |  |  |
|  | 467 | 482 |  |  |  |  |
| 742035 | 454 | 471 | GGCCGIGGCCGGIGCCGG | 68 | 32 | 84 |
|  | 460 | 477 |  |  |  |  |
|  | 466 | 483 |  |  |  |  |

Example 4: Antisense Inhibition of C9ORF72 Antisense Transcript with Oligonucleotides Antisense oligonucleotides (ASOs) described in Example 1 were tested for inhibition of C9ORF72 antisense transcript expression in vitro using a cell line in which a CMV promoter was installed to drive the expression of the endogenous C9ORF72 antisense gene via CRISPR/Cas9 technology.

The targeting portion of a single guide RNA (sgRNA) of the sequence 5'-GACAAGGGTACGTAATCTGTC-3', designated herein as SEQ ID NO: 97, was designed to target a site 1,020 base pairs downstream of the C9ORF72 hexanucleotide repeat. An NGG PAM motif is present at the 3' end of the target site. The targeting portion of the sgRNA was inserted into a dual-expression plasmid to generate the full-length sgRNA of the sequence: 5'-GACAAGGGTACG-TAATCTGTCTAGAGCTAGAAATAGCAAGT-TAAAATAAGGCTAGTCC GTTATCAACTT-GAAAAAGTGGCACCGAGTCGGTGCTTTTTT-3', designated herein as SEQ ID NO.: 101 and Cas9 nuclease.

The donor plasmid, containing a 922 base pair 5' homology arm, reverse CMV (CMVr), and 988 base pair 3' homology arm, was generated in pCR4 (Life Technologies) backbone plasmid by Gibson Assembly. The homology arm sequences were designed to center around the CRISPR/Cas9 cleavage site and were constructed using PCR primers: 5'-TAGTCCTGCAGGTTTAAACGAATTCGTGAGT-GAGGAGGCGGCA-3', forward primer, SEQ ID NO: 102, and 5'-AGCAGAGCTCAGATTACGTACCCTTGTTGT-GAACAAC-3', reverse primer, SEQ ID NO: 103, for the 5' arm; and 5'-CAATGTCAACGTCTGGCATTACTTC-TACTTTTG-3', forward primer, SEQ ID NO: 104, and 5'-TAGGGCGAATTGAATTTAGCGGCCGCACTGGCA-GGATCATAGC-3', reverse primer, SEQ ID NO: 105, for the 3' arm. The CMVr sequence was amplified from pCDNA3.1 using PCR primers: 5'-TACGTAATCT-GAGCTCTGCTTATATAGACC-3', forward primer, SEQ ID NO: 106, and 5'-AATGCCAGACGTTGACATTGATT-ATTGACTAGTTATTAATAG-3', reverse primer, SEQ ID NO: 107.

Neuroblast SH-SY5Y cells (Sigma-Aldrich) were cultured in a 1:1 mixture of MEM:F-12 (Life Technologies) supplemented with 10% FBS, 25 mM HEPES and Antibiotic-Antimycotic. C9orf72 CRISPR/Cas9 activity was assessed by measuring indel frequency using SURVEYOR mutation detection assay (Integrated DNA Technologies) with forward primer: 5'-GTTAGGCTCTGGGAGAG-TAGTTG-3', SEQ ID NO: 108, and reverse primer: 5'-CCTGGAGCAGGTAAATGCTGG-3', SEQ ID NO: 109. To generate SH-SY5Y cells expressing C9orf72 antisense transcript, SH-SY5Y cells were transfected with a plasmid expressing C9ORF72 CRISPR sgRNA and Cas9 and with a CMVr donor plasmid. Furthermore, the cells were co-transfected with a plasmid expressing EGFP, then single-cell sorted by FACS into 96-well plates. RT-qPCR was performed to screen for increased C9ORF72 antisense RNA. Positive clones were isolated and validated by PCR using primers inside CMVr and outside the 5' and 3' arms, respectively. Amplicons were further validated by sequencing to confirm on-target insertion of CMVr. Confirmation of single or double allele targeting was obtained by PCR with primers used in the SURVEYOR assay. Sequencing showed that the C9ORF72 antisense transcript contains 2 full hexanucleotide repeats.

The engineered SH-SY5Y cells were plated at 30,000 cells per well and electroporated at 140V with 10 μM ASO. 24 hours later cells were lysed. Strand specific RT-qPCR was performed on the isolated RNA, as described in Example 1, using the primer probe sets LTS01221 or C9ATS3'-1. The resulting normalized C9ORF72 antisense levels were then compared to the normalized values for C9ORF72 antisense transcript expression in control cells that were transfected with neither the C9ORF72 antisense plasmid nor an ASO. The results for each primer probe set are shown in the table below as percent inhibition of C9ORF72 antisense transcript expression relative to the control cells. A result of 0% inhibition indicates that the C9ORF72 antisense transcript levels were equal to that of control cells that were not transfected with an ASO. A negative value for % inhibition indicates that the C9ORF72 antisense transcript levels were higher than that of control cells that were not transfected with an ASO. A result of "n/a" indicates that the corresponding primer probe set was not used to analyze the indicated sample. The results show that many ASOs inhibited human C9ORF72 antisense transcript expression.

TABLE 9

Inhibition of C9ORF72 Antisense Transcript by Antisense Oligonucleotides

| Isis No. | LTS 01221 | C9ATS3'-1 | SEQ ID No. |
|---|---|---|---|
| 129700 | 22 | −4 | 29 |
| 687241 | 68 | n/a | 30 |
| 687242 | 60 | n/a | 31 |
| 687243 | 54 | n/a | 32 |
| 687244 | 47 | n/a | 33 |

TABLE 9-continued

Inhibition of C9ORF72 Antisense Transcript by Antisense Oligonucleotides

| Isis No. | LTS 01221 | C9ATS3'-1 | SEQ ID No. |
|---|---|---|---|
| 687245 | 53 | n/a | 34 |
| 687246 | 52 | n/a | 35 |
| 687247 | 53 | n/a | 36 |
| 687248 | 14 | n/a | 37 |
| 687249 | 6 | n/a | 38 |
| 687250 | 12 | n/a | 39 |
| 687251 | 53 | n/a | 40 |
| 687252 | 32 | n/a | 41 |
| 687253 | 21 | n/a | 42 |
| 687254 | 20 | n/a | 43 |
| 687255 | 81 | n/a | 44 |
| 687256 | 78 | n/a | 45 |
| 687257 | 63 | n/a | 46 |
| 687258 | 54 | n/a | 47 |
| 687259 | 52 | n/a | 48 |
| 687260 | 23 | n/a | 49 |
| 687261 | 9 | n/a | 50 |
| 687262 | 41 | n/a | 51 |
| 687263 | 24 | n/a | 52 |
| 687264 | 42 | n/a | 53 |
| 687265 | 25 | n/a | 54 |
| 687266 | 51 | n/a | 55 |
| 687267 | 20 | n/a | 56 |
| 687268 | 24 | n/a | 57 |
| 687269 | 20 | n/a | 58 |
| 687270 | 36 | n/a | 59 |
| 687271 | 10 | n/a | 60 |
| 687272 | 47 | n/a | 61 |
| 687273 | 50 | n/a | 62 |
| 687274 | 66 | n/a | 63 |
| 687275 | 42 | n/a | 64 |
| 687276 | 48 | n/a | 65 |
| 687277 | n/a | 40 | 66 |
| 687278 | n/a | 38 | 67 |
| 687279 | n/a | −24 | 68 |
| 687280 | n/a | 60 | 69 |
| 687281 | n/a | 69 | 70 |
| 687282 | n/a | 32 | 71 |
| 687283 | n/a | 69 | 72 |
| 687284 | n/a | 47 | 73 |
| 687285 | n/a | 28 | 74 |
| 687286 | n/a | 67 | 75 |
| 687287 | n/a | 71 | 76 |
| 687288 | n/a | 65 | 77 |
| 687289 | n/a | 63 | 78 |
| 687290 | 62 | 48 | 79 |
| 687291 | 75 | 71 | 80 |
| 687292 | 77 | 68 | 81 |
| 687293 | 76 | 72 | 82 |
| 742033 | 6 | 26 | 83 |

Example 5: Dose Dependent Inhibition of C9ORF72 Antisense Transcript with Oligonucleotides Isis Numbers 687241, 687255, 687256, 687280, 687281, 687283, 687286, 687287, 687288, 687289, 687291, 687292, and 687293 (see Example 1) were tested for dose dependent inhibition of C9ORF72 antisense transcript expression in vitro. The SH-SY5Y cells described in Example 4 were cultured at 30,000 cells per well and electroporated at 140 V treated with an oligonucleotide at a concentration listed in the tables below or they received no ASO as a control. 24 hours after electroporation, cells were lysed and total RNA was isolated and analyzed by RT-qPCR using primer probe set LTS01221 (Tables 10 and 11) or C9ATS3'-1 (Table 12). The results are shown below for each antisense oligonucleotide concentration, and half maximal inhibitory concentrations were calculated using Prism software (Graphpad).

TABLE 10

Dose Dependent C9ORF72 Antisense Transcript Inhibition

| Isis No. | Concentration (µM) | % Inhibition | IC$_{50}$ (µM) |
|---|---|---|---|
| 687241 | 0.625 | −5 | 3.49 |
|  | 1.25 | 17 |  |
|  | 2.5 | 34 |  |
|  | 5 | 52 |  |
|  | 10 | 66 |  |
|  | 20 | 54 |  |
| 687291 | 0.625 | 20 | 3.17 |
|  | 1.25 | 15 |  |
|  | 2.5 | 31 |  |
|  | 5 | 47 |  |
|  | 10 | 67 |  |
|  | 20 | 71 |  |

TABLE 11

Dose Dependent C9ORF72 Antisense Transcript Inhibition

| Isis No. | Dose (nM) | % Inhibition | IC$_{50}$ (µM) |
|---|---|---|---|
| 687255 | 0.625 | 9 | 2.34 |
|  | 1.25 | 20 |  |
|  | 2.5 | 39 |  |
|  | 5 | 57 |  |
|  | 10 | 62 |  |
|  | 20 | 69 |  |
| 687256 | 0.625 | 15 | 2.78 |
|  | 1.25 | 19 |  |
|  | 2.5 | 37 |  |
|  | 5 | 46 |  |
|  | 10 | 56 |  |
|  | 20 | 68 |  |
| 687291 | 0.625 | 24 | 1.72 |
|  | 1.25 | 24 |  |
|  | 2.5 | 41 |  |
|  | 5 | 63 |  |
|  | 10 | 62 |  |
|  | 20 | 70 |  |

TABLE 12

Dose Dependent C9ORF72 Antisense Transcript Inhibition

| Isis No. | Dose (nM) | % Inhibition | IC$_{50}$ (µM) |
|---|---|---|---|
| 687280 | 0.625 | 19 | 2.87 |
|  | 1.25 | 18 |  |
|  | 2.5 | 39 |  |
|  | 5 | 61 |  |
|  | 10 | 69 |  |
|  | 20 | 66 |  |
| 687281 | 0.625 | 13 | 5.21 |
|  | 1.25 | 12 |  |
|  | 2.5 | 26 |  |
|  | 5 | 39 |  |
|  | 10 | 60 |  |
|  | 20 | 69 |  |

TABLE 12-continued

Dose Dependent C9ORF72 Antisense Transcript Inhibition

| Isis No. | Dose (nM) | % Inhibition | IC$_{50}$ (µM) |
|---|---|---|---|
| 687283 | 0.625 | 16 | 4.98 |
| | 1.25 | 31 | |
| | 2.5 | 23 | |
| | 5 | 38 | |
| | 10 | 53 | |
| | 20 | 70 | |
| 687286 | 0.625 | −5 | 4.31 |
| | 1.25 | 8 | |
| | 2.5 | 29 | |
| | 5 | 51 | |
| | 10 | 65 | |
| | 20 | 71 | |
| 687287 | 0.625 | 5 | 3.10 |
| | 1.25 | 24 | |
| | 2.5 | 25 | |
| | 5 | 64 | |
| | 10 | 73 | |
| | 20 | 85 | |
| 687288 | 0.625 | 10 | 3.52 |
| | 1.25 | 12 | |
| | 2.5 | 31 | |
| | 5 | 58 | |
| | 10 | 66 | |
| | 20 | 78 | |
| 687289 | 0.625 | 14 | 5.43 |
| | 1.25 | 14 | |
| | 2.5 | 23 | |
| | 5 | 43 | |
| | 10 | 61 | |
| | 20 | 60 | |
| 687291 | 0.625 | 23 | 2.09 |
| | 1.25 | 33 | |
| | 2.5 | 35 | |
| | 5 | 67 | |
| | 10 | 75 | |
| | 20 | 77 | |
| 687292 | 0.625 | 19 | 3.94 |
| | 1.25 | 11 | |
| | 2.5 | 25 | |
| | 5 | 56 | |
| | 10 | 68 | |
| | 20 | 65 | |
| 687293 | 0.625 | 23 | 2.15 |
| | 1.25 | 25 | |
| | 2.5 | 44 | |
| | 5 | 63 | |
| | 10 | 77 | |
| | 20 | 75 | | fibroblast lines. The antisense oligonucleotides listed in Tables 13 and 14 below target the hexanucleotide repeat of the C9ORF72 antisense transcript. Each nucleoside of the antisense oligonucleotides in Table 13 below is modified with a 2'-MOE substitution. All of the cytosines are 5-methylcytosines, and all of the internucleoside linkages are phosphorothioate linkages. The motifs and internucleoside linkages of the oligonucleotides in Table 14 are shown in the table. The substitution or lack thereof at the 2'-position of each nucleoside is denoted as "d", meaning 2'-deoxy, or "e", meaning 2'-MOE. Each internucleoside linkage is denoted as "o", meaning phosphodiester, or "s", meaning phosphorothioate. All of the cytosines in Table 14 are 5-methylcytosines. The oligonucleotides in Table 14 also contain inosine residues, indicated by "I".

TABLE 13

Fully modified antisense oligonucleotides targeting the antisense transcript of C9ORF72

| Isis No. No. | Sequence | SEQ ID |
|---|---|---|
| 730389 | GGGGCCGGGGCCGGGGCC | 85 |
| 730390 | CGGGGCCGGGGCCGGGGC | 86 |
| 730391 | CCGGGGCCGGGGCCGGGG | 87 |
| 730392 | GCCGGGGCCGGGGCCGGG | 88 |
| 730393 | GGCCGGGGCCGGGGCCGG | 89 |
| 730394 | GGGCCGGGGCCGGGGCCG | 90 |
| 730395 | GGCCGGGGCCGGGGCC | 91 |
| 730396 | GGGCCGGGGCCGGGGC | 92 |
| 730397 | GGGGCCGGGGCCGGGG | 93 |
| 730398 | CGGGGCCGGGGCCGGG | 94 |
| 730399 | CCGGGGCCGGGGCCGG | 95 |
| 730400 | GCCGGGGCCGGGGCCG | 96 |

TABLE 14

Antisense oligonucleotides targeting the antisense transcript of C9ORF72

| Isis No. | Sequence (5' to 3') | Motif (5' to 3') | Internucleoside linkages (5' to 3') | SEQ ID No. |
|---|---|---|---|---|
| 737821 | CCGIGGCCGIGGCCGIGGCC | eeedeeeeedeeeeedeeee | ssosossssosossssososs | 98 |
| 742034 | GGCCGIGGCCGIGGCCGG | eeeeedeeeeedeeeeee | sssssosossssosossssss | 99 |

Example 6: Effect of Antisense Oligonucleotides Targeting C9ORF72 Antisense Transcript on RNA Foci Antisense oligonucleotides described above and those described in the tables below can be tested for their effects on C9ORF72 antisense foci in C9ORF72 ALS/FTD patient C9ORF72 antisense foci are visualized using fluorescent in situ hybridization with a fluorescently labeled Locked Nucleic Acid (LNA) probe targeting the hexanucleotide repeat containing C9ORF72 antisense transcript (Exiqon, Inc. Woburn Mass.). The sequence of the probe is presented in the table below. The probe was labeled with fluorescent 5' TYE-563. A 5' TYE-563-labeled fluorescent probe targeting CUG repeats is used as a negative control.

TABLE 15

LNA probes to the C9ORF72 antisense transcript containing the hexanucleotide repeat

| Target | Description of probe | Sequence | SEQ ID NO |
|---|---|---|---|
| GGCCCC Repeat of the Anti sense Transcript | Fluorescent LNA Probe | TYE563-GGGGCCGGGGCCGGGG | 93 |
| CUG Repeat | Fluorescent LNA Probe | TYE563-CAGCAGCAGCAGCAGCAGC | 100 |

All hybridization steps were performed under RNase-free conditions. Patient fibroblast cells were plated into chamber slides. 24 hours later, they were washed in PBS and transfected with 25 nM of an Isis antisense oligonucleotide in the table below or a negative control ASO that does not target any C9ORF72 RNA using 1 µl/ml Cytofectin transfection reagent (Genlantis, San Diego, Cat#T610001). Cells were incubated for 4 hours at 37° C. and 5% $CO_2$, before the medium was replaced with Dulbecco's modified Eagle medium (DMEM) supplemented with 20% tetracycline-free FBS and 2% penicillin/streptomycin and 1% amphotericin B. 24 hours after transfection, the cells were fixed in 4% PFA, then immediately permeabilized in 0.2% Triton X-100 (Sigma Aldrich #T-8787) in PBS for 10 minutes, washed twice in PBS for 5 minutes, dehydrated with ethanol, and air dried. The slides were heated in 400 µL hybridization buffer (50% deionized formamide, 2×SCC, 50 mM Sodium Phosphate, pH 7, and 10% dextran sulphate) at 66° C. for 20-60 minutes under floating RNase-free coverslips in a chamber humidified with hybridization buffer. Probes were denatured at 80° C. for 75 seconds and returned immediately to ice before diluting with hybridization buffer (40 nM final concentration). The incubating buffer was replaced with the probe-containing mix (400 µL per slide), and slides were hybridized under floating coverslips for 12-16 hours in a sealed, light-protected chamber.

After hybridization, floating coverslips were removed and slides were washed at room temperature in 0.1% Tween-20/2×SCC for 5 minutes before being subjected to three 10-minute stringency washes in 0.1×SCC at 65° C. The slides were then dehydrated through ethanol and air dried.

Primary visualization for quantification and imaging of foci was performed at 100× magnification using a Nikon Eclipse Ti confocal microscope system equipped with a Nikon CFI Apo TIRF 100× Oil objective (NA 1.49). Most foci are intra-nuclear but are also occasionally found in the cytoplasm. Treatment with RNase A, but not DNase I, eliminated the C9ORF72 antisense foci, demonstrating that they are comprised primarily of RNA. The foci in the fibroblasts were counted, and the data is presented in the table below as the number of foci per positive cell and the number of foci per cell overall. (A positive cell is a cell that has at least one focus.) The data in the table below show that treatment with the antisense oligonucleotides targeting the antisense C9ORF72 transcript, listed in the table below, decreased both the number of cells with at least one focus (foci per cell) and the number of foci within cells that still had at least one focus (foci per positive cell).

TABLE 16

Antisense C9ORF72 foci in patient fibroblasts

| Isis No. | Foci per positive cell | Foci per cell |
|---|---|---|
| Negative control ASO | 2.99 | 1.50 |
| 737821 | 2.73 | 1.00 |
| 742033 | 1.68 | 0.46 |
| 742034 | 1.38 | 0.22 |
| 742035 | 1.69 | 0.53 |

What is claimed is:

1. A compound comprising a modified oligonucleotide consisting of 16-30 linked nucleosides and having a nucleobase sequence comprising at least 16 contiguous nucleobases of a sequence selected from SEQ ID NO: 32, 33, 34 and 35, wherein the modified oligonucleotide comprises at least one modified internucleoside linkage and/or at least one modified sugar.

2. The compound of claim 1, wherein the modified oligonucleotide comprises at least one modified internucleoside linkage.

3. The compound of claim 2, wherein at least one modified internucleoside linkage is a phosphorothioate internucleoside linkage.

4. The compound of claim 2, wherein each internucleoside linkage is a phosphorothioate internucleoside linkage.

5. The compound of claim 3, wherein the modified oligonucleotide comprises at least one phosphodiester internucleoside linkage.

6. The compound of claim 1, wherein at least one nucleoside of the modified oligonucleotide comprises a modified nucleobase.

7. The compound of claim 6, wherein the at least one modified nucleobase is a hypoxanthine or 5-methylcytosine.

8. The compound of claim 1, wherein at least one nucleoside of the modified oligonucleotide comprises a modified sugar.

9. The compound of claim 8, wherein the at least one modified sugar is a bicyclic sugar.

10. The compound of claim 9, wherein the bicyclic sugar comprises a chemical bridge between the 2' and 4' position of the sugar, wherein the chemical bridge is selected from: 4'-CH$_2$—O-2'; 4'-CH(CH$_3$)—O-2'; 4'-(CH$_2$)$_2$—O-2'; and 4'-CH$_2$—N(R)—O-2' wherein R is, independently, H, C$_1$-C$_{12}$ alkyl, or a protecting group.

11. The compound of claim 8, wherein at least one modified sugar comprises a 2'-O-methoxyethyl group.

12. The compound of claim 1, wherein the modified oligonucleotide is a gapmer.

13. The compound of claim 1, wherein the modified oligonucleotide has a nucleobase sequence that is at least 90% complementary to the nucleobase sequences of SEQ ID NO: 13, when measured across the entire nucleobase sequence of the modified oligonucleotide.

14. The compound of claim 12, wherein the gapmer is selected from a 5-10-5 MOE gapmer, a 5-8-5 MOE gapmer, or a 4-8-4 MOE gapmer.

15. A compound comprising a modified oligonucleotide consisting of 16 to 30 linked nucleosides and having a nucleobase sequence comprising at least 16 contiguous nucleobases of the sequence of SEQ ID NO: 33, wherein the modified oligonucleotide comprises at least one modified internucleoside linkage and/or at least one modified sugar.

16. The compound of claim 15, wherein the modified oligonucleotide comprises at least one modified internucleoside linkage.

17. The compound of claim 16, wherein at least one modified internucleoside linkage is a phosphorothioate internucleoside linkage.

18. The compound of claim 16, wherein each internucleoside linkage is a phosphorothioate internucleoside linkage.

19. The compound of claim 17, wherein the modified oligonucleotide comprises at least one phosphodiester internucleoside linkage.

20. The compound of claim 15, wherein at least one nucleoside of the modified oligonucleotide comprises a modified nucleobase.

21. The compound of claim 20, wherein the at least one modified nucleobase is a hypoxanthine or 5-methylcytosine.

22. The compound of claim 15, wherein at least one nucleoside of the modified oligonucleotide comprises a modified sugar.

23. The compound of claim 22, wherein the at least one modified sugar is a bicyclic sugar.

24. The compound of claim 23, wherein the bicyclic sugar comprises a chemical bridge between the 2' and 4' position of the sugar, wherein the chemical bridge is selected from: 4'-$CH_2$—O-2'; 4'-$CH(CH_3)$—O-2'; 4'-$(CH_2)_2$—O-2'; and 4'-$CH_2$—N(R)—O-2' wherein R is, independently, H, $C_1$-$C_{12}$ alkyl, or a protecting group.

25. The compound of claim 22, wherein at least one modified sugar comprises a 2'-O-methoxyethyl group.

26. The compound of claim 15, wherein the modified oligonucleotide is a gapmer.

27. The compound of claim 15, wherein the modified oligonucleotide has a nucleobase sequence that is at least 90% complementary to the nucleobase sequences of SEQ ID NO: 13, when measured across the entire nucleobase sequence of the modified oligonucleotide.

28. The compound of claim 26, wherein the gapmer is selected from a 5-10-5 MOE gapmer, a 5-8-5 MOE gapmer, or a 4-8-4 MOE gapmer.

29. A compound comprising a modified oligonucleotide consisting of 16 to 30 linked nucleosides and having a nucleobase sequence comprising at least 16 contiguous nucleobases complementary to an equal length portion of nucleobases 608-636 of SEQ ID NO: 13, wherein the modified oligonucleotide comprises at least one modified internucleoside linkage and/or at least one modified sugar.

30. The compound of claim 29, wherein the modified oligonucleotide has a nucleobase sequence that is at least 90% complementary to the nucleobase sequence of SEQ ID NO: 13, when measured across the entire nucleobase sequence of the modified oligonucleotide.

31. The compound of claim 30, wherein at least one internucleoside linkage of the modified oligonucleotide is modified.

32. The compound of claim 31, wherein at least one modified internucleoside linkage is a phosphorothioate internucleoside linkage.

33. The compound of claim 30, wherein each internucleoside linkage is a phosphorothioate internucleoside linkage.

34. The compound of claim 32, wherein the modified oligonucleotide comprises at least one phosphodiester internucleoside linkage.

35. The compound of claim 30, wherein at least one nucleoside of the modified oligonucleotide comprises a modified nucleobase.

36. The compound of claim 35, wherein the at least one modified nucleobase is a hypoxanthine or a 5-methylcytosine.

37. The compound of claim 30, wherein the at least one nucleoside of the modified oligonucleotide comprises a modified sugar.

38. The compound of claim 37, wherein the at least one modified sugar is a bicyclic sugar.

39. The compound of claim 38, wherein the bicyclic sugar comprises a chemical bridge between the 2' and 4' position of the sugar, wherein the chemical bridge is selected from: 4'-$CH_2$—O-2'; 4'-$CH(CH_3)$—O-2'; 4'-$(CH_2)_2$—O-2'; and 4'-$CH_2$—N(R)—O-2' wherein R is, independently, H, $C_1$-$C_{12}$ alkyl, or a protecting group.

40. The compound of claim 37, wherein at least one modified sugar comprises a 2'-O-methoxyethyl group.

41. The compound of claim 30, wherein the modified oligonucleotide is a gapmer.

42. The compound of claim 41, wherein the gapmer is selected from a 5-10-5 MOE gapmer, a 5-8-5 MOE gapmer, or a 4-8-4 MOE gapmer.

* * * * *

SEQUENCE LISTING

<160> NUMBER OF SEQ ID NOS: 109

<210> SEQ ID NO 1
<211> LENGTH: 3339
<212> TYPE: DNA
<213> ORGANISM: Homo sapiens

<400> SEQUENCE: 1

```
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata    180
atgtgacagt tggaatgcag tgatgtcgac tctttgccca ccgccatctc cagctgttgc    240
caagacagag attgctttaa gtggcaaatc acctttatta gcagctactt ttgcttactg    300
ggacaatatt cttggtccta gagtaaggca catttgggct ccaaagacag aacaggtact    360
```

```
tctcagtgat ggagaaataa cttttcttgc caaccacact ctaaatggag aaatccttcg    420
aaatgcagag agtggtgcta tagatgtaaa gttttttgtc ttgtctgaaa agggagtgat    480
tattgtttca ttaatctttg atggaaactg gaatggggat cgcagcacat atggactatc    540
aattatactt ccacagacag aacttagttt ctacctccca cttcatagag tgtgtgttga    600
tagattaaca catataatcc ggaaaggaag aatatggatg cataaggaaa gacaagaaaa    660
tgtccagaag attatcttag aaggcacaga gagaatggaa gatcagggtc agagtattat    720
tccaatgctt actggagaag tgattcctgt aatggaactg ctttcatcta tgaaatcaca    780
cagtgttcct gaagaaatag atatagctga tacagtactc aatgatgatg atattggtga    840
cagctgtcat gaaggctttc ttctcaatgc catcagctca cacttgcaaa cctgtggctg    900
ttccgttgta gtaggtagca gtgcagagaa agtaaataag atagtcagaa cattatgcct    960
ttttctgact ccagcagaga gaaaatgctc caggttatgt gaagcagaat catcatttaa   1020
atatgagtca gggctctttg tacaaggcct gctaaaggat tcaactggaa gctttgtgct   1080
gcctttccgg caagtcatgt atgctccata tcccaccaca cacatagatg tggatgtcaa   1140
tactgtgaag cagatgccac cctgtcatga acatatttat aatcagcgta gatacatgag   1200
atccgagctg acagccttct ggagagccac ttcagaagaa gacatggctc aggatacgat   1260
catctacact gacgaaagct ttactcctga tttgaatatt tttcaagatg tcttacacag   1320
agacactcta gtgaaagcct tcctggatca ggtcttccag ctgaaacctg cttatctct    1380
cagaagtact ttccttgcac agtttctact tgtccttcac agaaaagcct tgacactaat   1440
aaaatatata gaagacgata cgcagaaggg aaaaaagccc tttaaatctc ttcggaacct   1500
gaagatagac cttgatttaa cagcagaggg cgatcttaac ataataatgg ctctggctga   1560
gaaaattaaa ccaggcctac actctttat ctttggaaga cctttctaca ctagtgtgca   1620
agaacgagat gttctaatga cttttttaaat gtgtaactta ataagcctat tccatcacaa   1680
tcatgatcgc tggtaaagta gctcagtggt gtggggaaac gttcccctgg atcatactcc   1740
agaattctgc tctcagcaat tgcagttaag taagttacac tacagttctc acaagagcct   1800
gtgagggat gtcaggtgca tcattacatt gggtgtctct tttcctagat ttatgctttt    1860
gggatacaga cctatgttta caatataata aatattattg ctatctttta aagatataat   1920
aataggatgt aaacttgacc acaactactg ttttttttgaa atacatgatt catgttttac   1980
atgtgtcaag gtgaaatctg agttggcttt tacagatagt tgactttcta tcttttggca   2040
ttctttggtg tgtagaatta ctgtaatact tctgcaatca actgaaaact agagcctta    2100
aatgatttca attccacaga agaaagtga gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa   2280
ccacagttag ggtgttttgt ttattttatt gttcttgcta ttgttgatat tctatgtagt   2340
tgagctctgt aaaaggaaat tgtatttat gttttagtaa ttgttgccaa cttttttaaat   2400
taattttcat tattttgag ccaaattgaa atgtgcacct cctgtgcctt ttttctcctt    2460
agaaaatcta attacttgga acaagttcag atttcactgg tcagtcattt tcatcttgtt   2520
ttcttcttgc taagtcttac catgtacctg ctttggcaat cattgcaact ctgagattat   2580
aaaatgcctt agagaatata ctaactaata agatcttttt ttcagaaaca gaaaatagtt   2640
ccttgagtac ttccttcttg catttctgcc tatgttttg aagttgttgc tgtttgcctg    2700
caataggcta taaggaatag caggagaaat tttactgaag tgctgttttc ctaggtgcta   2760
```

```
ctttggcaga gctaagttat cttttgtttt cttaatgcgt ttggaccatt ttgctggcta      2820
taaaataact gattaatata attctaacac aatgttgaca ttgtagttac acaaacacaa      2880
ataaatattt tatttaaaat tctggaagta atataaaagg gaaatatat  ttataagaaa      2940 gggataaagg taatagagcc cttctgcccc ccacccacca aatttacaca acaaaatgac      3000
atgttcgaat gtgaaaggtc ataatagctt tcccatcatg aatcagaaag atgtggacag      3060
cttgatgttt tagacaacca ctgaactaga tgactgttgt actgtagctc agtcatttaa      3120
aaaatatata aatactacct tgtagtgtcc catactgtgt tttttacatg gtagattctt      3180
atttaagtgc taactggtta ttttctttgg ctggtttatt gtactgttat acagaatgta      3240
agttgtacag tgaaataagt tattaaagca tgtgtaaaca ttgttatata tcttttctcc      3300
taaatggaga attttgaata aaatatattt gaaattttg                            3339

<210> SEQ ID NO 2
<211> LENGTH: 30001
<212> TYPE: DNA
<213> ORGANISM: Homo sapiens

<400> SEQUENCE: 2
caaagaaaag ggggaggttt tgttaaaaaa gagaaatgtt acatagtgct ctttgagaaa        60
attcattggc actattaagg atctgaggag ctggtgagtt tcaactgtg  agtgatggtg       120 gtagataaaa ttagagctgc agcaggtcat tttagcaact attagataaa actggtctca       180
ggtcacaacg ggcagttgca gcagctggac ttggagagaa ttacactgtg ggagcagtgt       240
catttgtcct aagtgctttt ctaccccta  cccccactat tttagttggg tataaaaga        300 atgacccaat ttgtatgatc aactttcaca aagcatagaa cagtaggaaa agggtctgtt       360
tctgcagaag gtgtagacgt tgagagccat tttgtgtatt tattcctccc tttcttcctc       420
ggtgaatgat taaaacgttc tgtgtgattt ttagtgatga aaaagattaa atgctactca       480
ctgtagtaag tgccatctca cacttgcaga tcaaaaggca cacagtttaa aaaacctttg       540
tttttttaca catctgagtg gtgtaaatgc tactcatctg tagtaagtgg aatctataca       600
cctgcagacc aaaagacgca aggtttcaaa aatctttgtg ttttttacac atcaaacaga       660
atggtacgtt tttcaaaagt taaaaaaaaa caactcatcc acatattgca actagcaaaa       720
atgacattcc ccagtgtgaa aatcatgctt gagagaattc ttacatgtaa aggcaaaatt       780
gcgatgactt tgcaggggac cgtgggattc ccgcccgcag tgccggagct gtcccctacc       840
agggtttgca gtggagtttt gaatgcactt aacagtgtct tacggtaaaa acaaaatttc       900
atccaccaat tatgtgttga gcgcccactg cctaccaagc acaaacaaaa ccattcaaaa       960
ccacgaaatc gtcttcactt tctccagatc cagcagcctc ccctattaag gttcgcacac      1020
gctattgcgc caacgctcct ccagagcggg tcttaagata aagaacagg  acaagttgcc      1080 ccgccccatt tcgctagcct cgtgagaaaa cgtcatcgca catagaaaac agacagacgt      1140
aacctacggt gtcccgctag gaaagagagg tgcgtcaaac agcgacaagt tccgcccacg      1200
taaaagatga cgcttggtgt gtcagccgtc cctgctgccc ggttgcttct cttttgggggg    1260 cggggtctag caagagcagg tgtgggttta ggaggtgtgt gttttttgttt ttcccaccct    1320 ctctccccac tacttgctct cacagtactc gctgagggtg aacaagaaaa gacctgataa     1380
agattaacca gaagaaaaca aggagggaaa caaccgcagc ctgtagcaag ctctggaact    1440
caggagtcgc gcgctagggg ccggggccgg ggccggggcg tggtcggggc gggcccgggg    1500
```

```
gcgggcccgg ggcggggctg cggttgcggt gcctgcgccc gcggcggcgg aggcgcaggc    1560
ggtggcgagt gggtgagtga ggaggcggca tcctggcggg tggctgtttg gggttcggct    1620
gccgggaaga ggcgcgggta aagcgggggg ctctcctcag agctcgacgc attttttactt   1680 tccctctcat ttctctgacc gaagctgggg gtcgggcttt cgcctctagc gactggtgga    1740
attgcctgca tccgggcccc gggcttcccg gcggcggcgg cggcggcggc ggcgcaggga    1800
caagggatgg ggatctggcc tcttccttgc tttcccgccc tcagtacccg agctgtctcc    1860
ttcccgggga cccgctggga gcgctgccgc tgcgggctcg agaaaaggga gcctcgggta    1920
ctgagaggcc tcgcctgggg gaaggccgga gggtgggcgg cgcgcggctt ctgcggacca    1980
agtcggggtt cgctaggaac ccgagacggt ccctgccggc gaggagatca tgcgggatga    2040 gatggggtg tggagacgcc tgcacaattt cagcccaagc ttctagagag tggtgatgac      2100
ttgcatatga gggcagcaat gcaagtcggt gtgctcccca ttctgtggga catgacctgg    2160
ttgcttcaca gctccagat gacacagact tgcttaaagg aagtgactat tgtgacttgg      2220
gcatcacttg actgatggta atcagttgtc taaagaagtg cacagattac atgtccgtgt    2280
gctcattggg tctatctggc cgcgttgaac accaccaggc tttgtattca gaaacaggag    2340
ggaggtcctg cactttccca ggaggggtgg ccctttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact     2580
tttaacataa tctgtgaata tcacagaaac aagactatca tatagggat attaataacc     2640 tggagtcaga atacttgaaa tacggtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctcttttgggc tgggagaaaa taaacagcat ggttacaagt   3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaatttc actacaatag cagtggacca accacctttc      3600
taaataccaa tcagggaaga gatggttgat ttttaacag acgtttaaag aaaaagcaaa      3660 acctcaaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatctcgg cttccctcaa aagactggct aatgtttggt    3840
aactctctgg agtagacagc actacatgta cgtaagatag gtacataaac aactattggt    3900
```

```
tttgagctga ttttttttcag ctgcatttgc atgtatggat ttttctcacc aaagacgatg   3960
acttcaagta ttagtaaaat aattgtacag ctctcctgat tatacttctc tgtgacattt   4020
catttcccag gctatttctt ttggtaggat ttaaaactaa gcaattcagt atgatctttg   4080
tccttcattt tcttttcttat tcttttttgtt tgtttgtttg tttgttttttt tcttgaggca   4140 gagtctctct ctgtcgccca ggctggagtg cagtggcgcc atctcagctc attgcaacct   4200
ctgccacctc cgggttcaag agattctcct gcctcagcct cccgagtagc tgggattaca   4260
ggtgtccacc accacacccg ctaattttt tgtattttta gtagaggtgg ggtttcacca   4320
tgttggccag gctggtcttg agctcctgac ctcaggtgat ccacctgcct cggcctacca   4380
aagagctggg ataacaggtg tgacccacca tgcccggccc attttttttt tcttattctg   4440
ttaggagtga gagtgtaact agcagtataa tagttcaatt ttcacaacgt ggtaaaagtt   4500
tccctataat tcaatcagat tttgctccag ggttcagttc tgttttagga aatactttta   4560
ttttcagttt aatgatgaaa tattagagtt gtaatattgc ctttatgatt atccaccttt   4620
ttaacctaaa agaatgaaag aaaaatatgt ttgcaatata atttttatggt tgtatgttaa   4680 cttaattcat tatgttggcc tccagtttgc tgttgttagt tatgacagca gtagtgtcat   4740
taccatttca attcagatta cattcctata tttgatcatt gtaaactgac tgcttacatt   4800
gtattaaaaa cagtggatat tttaaagaag ctgtacggct tatatctagt gctgtctctt   4860
aagactatta aattgataca acatatttaa aagtaaatat tacctaaatg aattttttgaa   4920 attacaaata cacgtgttaa aactgtcgtt gtgttcaacc atttctgtac atacttagag   4980
ttaactgttt tgccaggctc tgtatgccta ctcataatat gataaaagca ctcatctaat   5040
gctctgtaaa tagaagtcag tgcttttccat cagactgaac tctcttgaca agatgtggat   5100
gaaattcttt aagtaaaatt gtttactttg tcatacattt acagatcaaa tgttagctcc   5160
caaagcaatc atatggcaaa gataggtata tcatagtttg cctattagct gctttgtatt   5220
gctattatta taaatagact tcacagtttt agacttgctt aggtgaaatt gcaattcttt   5280
ttactttcag tcttagataa caagtcttca attatagtac aatcacacat tgcttaggaa   5340
tgcatcatta ggcgattttg tcattatgca aacatcatag agtgtactta cacaaaccta   5400
gatagtatag cctttatgta cctaggccgt atggtatagt ctgttgctcc taggccacaa   5460
acctgtacaa ctgttactgt actgaatact atagacagtt gtaacacagt ggtaaatatt   5520
tatctaaata tatgcaaaca gagaaaaggt acagtaaaag tatggtataa aagataatgg   5580
tatacctgtg taggccactt accacgaatg gagcttgcag gactagaagt tgctctgggt   5640
gagtcagtga gtgagtggtg aattaatgtg aaggcctaga acactgtaca ccactgtaga   5700
ctataaacac agtacgctga agctacacca aatttatctt aacagttttt cttcaataaa   5760
aaattataac ttttttaactt tgtaaacttt ttaatttttt aacttttaaa atacttagct   5820
tgaaacacaa atacattgta tagctataca aaaatattt ttctttgtat ccttattcta   5880
gaagcttttt tctatttttct atttttaaatt tttttttta cttgttagtc gttttttgtta   5940 aaaactaaaa cacacacact ttcacctagg catagacagg attaggatca tcagtatcac   6000
tcccttccac ctcactgcct tccacctcca catcttgtcc cactggaagg ttttttaggg   6060
caataacaca catgtagctg tcacctatga taacagtgct ttctgttgaa tacctcctga   6120
aggacttgcc tgaggctgtt ttacatttaa cttaaaaaaa aaaaagtag aaggagtgca   6180 ctctaaaata acaataaaag gcatagtata gtgaatacat aaaccagcaa tgtagtagtt   6240
```

```
tattatcaag tgttgtacac tgtaataatt gtatgtgcta tactttaaat aacttgcaaa       6300
atagtactaa gaccttatga tggttacagt gtcactaagg caatagcata ttttcaggtc       6360
cattgtaatc taatgggact accatcatat atgcagtcta ccattgactg aaacgttaca       6420
tggcacataa ctgtatttgc aagaatgatt tgttttacat taatatcaca taggatgtac       6480 cttttagag tggtatgttt atgtggatta agatgtacaa gttgagcaag gggaccaaga        6540
gccctgggtt ctgtcttgga tgtgagcgtt tatgttcttc tcctcatgtc tgttttctca       6600
ttaaattcaa aggcttgaac gggccctatt tagcccttct gttttctacg tgttctaaat       6660
aactaaagct tttaaattct agccatttag tgtagaactc tctttgcagt gatgaaatgc       6720
tgtattggtt tcttggctag catattaaat attttatct ttgtcttgat acttcaatgt        6780
cgttttaaac atcaggatcg ggcttcagta ttctcataac cagagagttc actgaggata       6840
caggactgtt tgcccatttt ttgttatggc tccagacttg tggtatttcc atgtcttttt       6900
tttttttttt tttttgacc ttttagcggc tttaaagtat ttctgttgtt aggtgttgta       6960
ttacttttct aagattactt aacaaagcac cacaaactga gtggctttaa acaacagcaa       7020
tttattctct cacaattcta gaagctagaa gtccgaaatc aaagtgttga caggggcatg       7080
atcttcaaga gagaagactc tttccttgcc tcttcctggc ttctggtggt taccagcaat       7140
cctgagtgtt cctttcttgc cttgtagttt caacaatcca gtatctgcct tttgtcttca       7200
catggctgtc taccatttgt ctctgtgtct ccaaatctct ctccttataa acacagcagt       7260
tattggatta ggccccactc taatccagta tgaccccatt ttaacatgat tacacttatt       7320
tctagataag gtcacattca cgtacaccaa gggttaggaa ttgaacatat cttttgggg       7380 gacacaattc aacccacaag tgtcagtctc tagctgagcc tttcccttcc tgttttctc       7440 ctttttagtt gctatgggtt aggggccaaa tctccagtca tactagaatt gcacatggac       7500
tggatatttg ggaatactgc gggtctattc tatgagcttt agtatgtaac atttaatatc       7560
agtgtaaaga agccctttt taagttattt ctttgaattt ctaaatgtat gccctgaata        7620
taagtaacaa gttaccatgt cttgtaaaat gatcatatca acaaacattt aatgtgcacc       7680
tactgtgcta gttgaatgtc tttatcctga taggagataa caggattcca catctttgac      7740
ttaagaggac aaaccaaata tgtctaaatc atttggggtt ttgatggata tctttaaatt      7800
gctgaaccta atcattggtt tcatatgtca ttgtttagat atctccggag catttggata      7860
atgtgacagt tggaatgcag tgatgtcgac tctttgccca ccgccatctc cagctgttgc      7920
caagacagag attgctttaa gtggcaaatc acctttatta gcagctactt ttgcttactg      7980
ggacaatatt cttggtccta gagtaaggca catttgggct ccaaagacag aacaggtact      8040
tctcagtgat ggagaaataa cttttcttgc caaccacact ctaaatggag aaatccttcg      8100
aaatgcagag agtggtgcta tagatgtaaa gttttttgtc ttgtctgaaa agggagtgat      8160
tattgtttca ttaatctttg atggaaactg gaatggggat cgcagcacat atggactatc      8220
aattatactt ccacagacag aacttagttt ctacctccca cttcatagag tgtgtgttga      8280
tagattaaca catataatcc ggaaaggaag aatatggatg cataaggtaa gtgattttc       8340 agcttattaa tcatgttaac ctatctgttg aaagcttatt ttctggtaca tataaatctt      8400 attttttaa ttatatgcag tgaacatcaa acaataaatg ttatttattt tgcatttacc       8460
ctattagata caaatacatc tggtctgata cctgtcatct tcatattaac gtgggaaggt      8520
acgaaatggt agctccacat tatagatgaa aagctaaagc ttagacaaat aaagaaactt      8580
ttagaccctg gattcttctt gggagccttt gactctaata ccttttgttt cccttttcatt    8640
```

```
gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat ttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc tttttgaaac tatgcagatg ttacattgac tgttttctgt    9180
gaagttatct tttttcact gcagaataaa ggttgttttg attttatttt gtattgttta    9240
tgagaacatg catttgttgg gttaatttcc taccccctgcc cccatttttt ccctaaagta    9300
gaaagtattt ttcttgtgaa ctaaattact acacaagaac atgtctattg aaaaataagc    9360
aagtatcaaa atgttgtggg ttgtttttt aaataaattt tctcttgctc aggaaagaca    9420
agaaaatgtc cagaagatta tcttagaagg cacagagaga atggaagatc aggtatatgc    9480
aaattgcata ctgtcaaatg ttttctcac agcatgtatc tgtataaggt tgatggctac    9540
atttgtcaag gccttggaga catacgaata agcctttaat ggagcttta tggaggtgta    9600 cagaataaac tggaggaaga tttccatatc ttaaacccaa agagttaaat cagtaaacaa    9660
aggaaaatag taattgcatc tacaaattaa tatttgctcc ctttttttt ctgtttgccc    9720 agaataaatt ttggataact tgttcatagt aaaaataaaa aaaattgtct ctgatatgtt    9780
ctttaaggta ctacttctcg aacctttccc tagaagtagc tgtaacagaa ggagagcata    9840
tgtacccctg aggtatctgt ctggggtgta ggcccaggtc cacacaatat ttcttctaag    9900
tcttatgttg tatcgttaag actcatgcaa tttacatttt attccataac tatttagta    9960 ttaaaattg tcagtgatat ttcttaccct ctcctctagg aaaatgtgcc atgtttatcc   10020
cttggctttg aatgccctc aggaacagac actaagagtt tgagaagcat ggttacaagg   10080
gtgtggcttc ccctgcggaa actaagtaca gactatttca ctgtaaagca gagaagttct   10140
tttgaaggag aatctccagt gaagaaagag ttcttcactt ttacttccat ttcctcttgt   10200
gggtgaccct caatgctcct tgtaaaactc caatatttta aacatggctg ttttgccttt   10260
ctttgcttct ttttagcatg aatgagacag atgatacttt aaaaaagtaa ttaaaaaaaa   10320
aaacttgtga aaatacatgg ccataataca gaacccaata caatgatctc ctttaccaaa   10380
ttgttatgtt tgtacttttg tagatagctt tccaattcag agacagttat tctgtgtaaa   10440
ggtctgactt aacaagaaaa gatttcccctt tacccaaaga atcccagtcc ttatttgctg   10500
gtcaataagc agggtcccca ggaatggggt aactttcagc accctctaac ccactagtta   10560
ttagtagact aattaagtaa acttatcgca agttgaggaa acttagaacc aactaaaatt   10620
ctgcttttac tgggattttg ttttttcaaa ccagaaacct ttacttaagt tgactactat   10680
taatgaattt tggtctctct tttaagtgct cttcttaaaa atgttatctt actgctgaga   10740
agttcaagtt tgggaagtac aaggaggaat agaaacttaa gagattttct tttagagcct   10800
cttctgtatt tagccctgta ggattttttt tttttttttt tttttggtg ttgttgagct   10860 tcagtgaggc tattcattca cttatactga taatgtctga gatactgtga atgaaatact   10920
atgtatgctt aaacctaaga ggaaatattt tcccaaaatt attcttcccg aaaaggagga   10980
```

```
gttgccttt    gattgagttc   ttgcaaatct   cacaacgact   ttattttgaa   caatactgtt   11040
tggggatgat   gcattagttt   gaaacaactt   cagttgtagc   tgtcatctga   taaaattgct   11100
tcacagggaa   ggaaatttaa   cacggatcta   gtcattattc   ttgttagatt   gaatgtgtga   11160
attgtaattg   taaacaggca   tgataattat   tactttaaaa   actaaaaaca   gtgaatagtt   11220
agttgtggag   gttactaaag   gatggttttt   ttttaaataa   aactttcagc   attatgcaaa   11280
tgggcatatg   gcttaggata   aaacttccag   aagtagcatc   acatttaaat   tctcaagcaa   11340
cttaataata   tggggctctg   aaaaactggt   taaggttact   ccaaaaatgg   ccctgggtct   11400
gacaaagatt   ctaacttaaa   gatgcttatg   aagactttga   gtaaaatcat   ttcataaaat   11460
aagtgaggaa   aaacaactag   tattaaattc   atcttaaata   atgtatgatt   taaaaaatat   11520
gtttagctaa   aaatgcatag   tcatttgaca   atttcattta   tatctcaaaa   aatttactta   11580
accaagttgg   tcacaaaact   gatgagactg   gtggtggtag   tgaataaatg   agggaccatc   11640
catatttgag   acactttaca   tttgtgatgt   gttatactga   attttcagtt   tgattctata   11700
gactacaaat   ttcaaaatta   caatttcaag   atgtaataag   tagtaaatc   ttgaaatagc   11760
tctaaaggga   atttttctgt   tttattgatt   cttaaaatat   atgtgctgat   tttgatttgc   11820
atttgggtag   attatacttt   tatgagtatg   gaggttaggt   attgattcaa   gttttcctta   11880
cctatttggt   aaggatttca   aagtcttttt   gtgcttggtt   ttcctcattt   ttaaatatga   11940
aatatattga   tgacctttaa   caaattttt   ttatctcaaa   ttttaaagga   gatcttttct   12000
aaaagaggca   tgatgactta   atcattgcat   gtaacagtaa   acgataaacc   aatgattcca   12060
tactctctaa   agaataaaag   tgagctttag   ggccgggcat   ggtcagaaat   ttgacaccaa   12120
cctggccaac   atggcgaaac   cccgtctcta   ctaaaaatac   aaaaatcagc   cgggcatggt   12180
ggcggcacct   atagtcccag   ctacttggga   ggatgagaca   ggagagtcac   ttgaacctgg   12240
gaggagaggt   tgcagtgagc   tgagatcacg   ccattgcact   ccagcctgag   caatgaaagc   12300
aaaactccat   ctcaaaaaaa   aaaaagaaa   agaaagaata   aaagtgagct   ttggattgca   12360
tataaatcct   ttagacatgt   agtagacttg   tttgatactg   tgtttgaaca   aattacgaag   12420
tattttcatc   aaagaatgtt   attgtttgat   gttatttta   tttttttattg   cccagcttct   12480
ctcatattac   gtgattttct   tcacttcatg   tcactttatt   gtgcagggtc   agagtattat   12540
tccaatgctt   actggagaag   tgattcctgt   aatggaactg   ctttcatcta   tgaaatcaca   12600
cagtgttcct   gaagaaatag   atgtaagttt   aaatgagagc   aattatacac   tttatgagtt   12660
ttttgggggtt   atagtattat   tatgtatatt   attaatattc   taattttaat   agtaaggact   12720
ttgtcataca   tactattcac   atacagtatt   agccacttta   gcaaataagc   acacacaaaa   12780
tcctggattt   tatggcaaaa   cagaggcatt   tttgatcagt   gatgacaaaa   ttaaattcat   12840
tttgtttatt   tcattacttt   tataattcct   aaaagtggga   ggatcccagc   tcttatagga   12900
gcaattaata   tttaatgtag   tgtcttttga   aacaaaactg   tgtgccaaag   tagtaaccat   12960
taatggaagt   ttacttgtag   tcacaaattt   agtttcctta   atcatttgtt   gaggacgttt   13020
tgaatcacac   actatgagtg   ttaagagata   cctttaggaa   actattcttg   ttgttttctg   13080
attttgtcat   ttaggttagt   ctcctgattc   tgacagctca   gaagaggaag   ttgttcttgt   13140
aaaaattgtt   taacctgctt   gaccagcttt   cacatttgtt   cttctgaagt   ttatggtagt   13200
gcacagagat   tgttttttgg   gggagtcttga   ttctcggaaa   tgaaggcagt   gtgttatatt   13260
gaatccgagc   ttccgaaaac   ttgtatatta   aaagtgttat   ttcaacacta   tgttacagcc   13320
agactaattt   ttttatttt   tgatgcattt   tagatagctg   atacagtact   caatgatgat   13380
```

```
gatattggtg acagctgtca tgaaggcttt cttctcaagt aagaattttt cttttcataa    13440
aagctggatg aagcagatac catcttatgc tcacctatga caagatttgg aagaaagaaa    13500
ataacagact gtctacttag attgttctag ggacattacg tatttgaact gttgcttaaa    13560
tttgtgttat ttttcactca ttatatttct atatatattt ggtgttattc catttgctat    13620
ttaaagaaac cgagtttcca tcccagacaa gaaatcatgg ccccttgctt gattctggtt    13680
tcttgtttta cttctcatta aagctaacag aatcctttca tattaagttg tactgtagat    13740
gaacttaagt tatttaggcg tagaacaaaa ttattcatat ttatactgat cttttttccat   13800 ccagcagtgg agtttagtac ttaagagttt gtgcccttaa accagactcc ctggattaat    13860
gctgtgtacc cgtgggcaag gtgcctgaat tctctataca cctatttcct catctgtaaa    13920
atggcaataa tagtaatagt acctaatgtg tagggttgtt ataagcattg agtaagataa    13980
ataatataaa gcacttagaa cagtgcctgg aacataaaaa cacttaataa tagctcatag    14040
ctaacatttc ctatttacat ttcttctaga aatagccagt atttgttgag tgcctacatg    14100
ttagttcctt tactagttgc tttacatgta ttatcttata ttctgtttta aagtttcttc    14160
acagttacag atttttcatga aatttttactt ttaataaaag agaagtaaaa gtataaagta  14220 ttcacttta tgttcacagt cttttccttt aggctcatga tggagtatca gaggcatgag     14280
tgtgtttaac ctaagagcct taatggcttg aatcagaagc actttagtcc tgtatctgtt    14340
cagtgtcagc ctttcataca tcattttaaa tcccatttga ctttaagtaa gtcacttaat    14400
ctctctacat gtcaatttct tcagctataa aatgatggta tttcaataaa taaatacatt    14460
aattaaatga tattatactg actaattggg ctgttttaag gctcaataag aaaatttctg    14520
tgaaaggtct ctagaaaatg taggttccta tacaaataaa agataacatt gtgcttatag    14580
cttcggtgtt tatcatataa agctattctg agttatttga agagctcacc tactttttt     14640 tgttttagt ttgttaaatt gttttatagg caatgttttt aatctgtttt ctttaactta     14700
cagtgccatc agctcacact tgcaaacctg tggctgttcc gttgtagtag gtagcagtgc    14760
agagaaagta aataaggtag tttattttat aatctagcaa atgatttgac tctttaagac    14820
tgatgatata tcatggattg tcatttaaat ggtaggttgc aattaaaatg atctagtagt    14880
ataaggaggc aatgtaatct catcaaattg ctaagacacc ttgtggcaac agtgagtttg    14940 aaatataactg agtaagaatc atttatcagt ttatttgat agctcggaaa taccagtgtc    15000
agtagtgtat aaatggtttt gagaatatat taaaatcaga tatataaaaa aaattactct    15060
tctatttccc aatgttatct ttaacaaatc tgaagatagt catgtacttt ggtagtagt     15120 tccaaagaaa tgttatttgt ttattcatct tgatttcatt gtcttcgctt tccttctaaa    15180
tctgtccctt ctagggagct attgggatta agtggtcatt gattattata ctttattcag    15240
taatgtttct gacccttttcc ttcagtgcta cttgagttaa ttaaggatta atgaacagtt   15300
acatttccaa gcattagcta ataaactaaa ggattttgca ctttttcttca ctgaccatta   15360 gttagaaaga gttcagagat aagtatgtgt atctttcaat ttcagcaaac ctaattttt     15420 aaaaaaagtt ttacatagga aatatgttgg aaatgatact ttacaaagat attcataatt    15480 ttttttttgta atcagctact ttgtatattt acatgagcct taatttatat ttctcatata   15540
accatttatg agagcttagt ataacctgtgt cattatattg catctacgaa ctagtgacct   15600
tattccttct gttacctcaa acaggtggct ttccatctgt gatctccaaa gccttaggtt    15660
gcacagagtg actgccgagc tgctttatga agggagaaag gctccatagt tggagtgttt    15720
```

```
tttttttttt ttttaaacat ttttcccatc ctccatcctc ttgagggaga atagcttacc    15780
ttttatcttg ttttaatttg agaaagaagt tgccaccact ctaggttgaa aaccactcct    15840
ttaacataat aactgtggat atggtttgaa tttcaagata gttacatgcc ttttttatttt   15900 tcctaataga gctgtaggtc aaatattatt agaatcagat ttctaaatcc cacccaatga    15960
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcacct gaagagtcac    16140
agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtctttttac ttcatgtttt aatgctaaaa    16380
tattttcttt tatagatagt cagaacatta tgcctttttc tgactccagc agagagaaaa    16440
tgctccaggt tatgtgaagc agaatcatca tttaaatatg agtcagggct ctttgtacaa    16500
ggcctgctaa aggtatagtt tctagttatc acaagtgaaa ccacttttct aaaatcattt    16560
ttgagactct ttatagacaa atcttaaata ttagcatttta atgtatctca tattgacatg    16620
cccagagact gacttccttt acacagttct gcacatagac tatatgtctt atggatttat    16680
agttagtatc atcagtgaaa caccatagaa tacccttttgt gttccaggtg ggtccctgtt    16740
cctacatgtc tagcctcagg actttttttt tttaacaca tgcttaaatc aggttgcaca    16800
tcaaaaataa gatcatttct ttttaactaa atagatttga attttattga aaaaaaattt    16860
taaacatctt taagaagctt ataggattta agcaattcct atgtatgtgt actaaaatat    16920
atatatttct atatataata tatattagaa aaaaattgta ttttttcttt atttgagtct    16980
actgtcaagg agcaaaacag agaaatgtaa attagcaatt atttataata cttaaaggga    17040
agaaagttgt tcaccttgtt gaatctatta ttgttatttc aattatagtc ccaagacgtg    17100
aagaaatagc tttcctaatg gttatgtgat tgtctcatag tgactacttt cttgaggatg    17160
tagccacggc aaaatgaaat aaaaaaattt aaaaattgtt gcaaatacaa gttatattag    17220
gcttttgtgc attttcaata atgtgctgct atgaactcag aatgatagta tttaaatata    17280
gaaactagtt aaaggaaacg tagtttctat ttgagttata catatctgta aattagaact    17340
tctcctgtta aaggcataat aaaagtgctta atacttttgt ttcctcagca ccctctcatt    17400
taattatata attttagttc tgaaagggac ctataccaga tgcctagagg aaatttcaaa    17460
actatgatct aatgaaaaaa tatttaatag ttctccatgc aaatacaaat catatagttt    17520
tccagaaaat acctttgaca ttatacaaag atgattatca cagcattata atagtaaaaa    17580
aatggaaata gcctctttct tctgttctgt tcatagcaca gtgcctcata cgcagtaggt    17640
tattattaca tggtaactgg ctaccccaac tgattaggaa agaagtaaat ttgttttata    17700
aaaatacata ctcattgagg tgcatagaat aattaagaaa ttaaagacaa cttgtaattt    17760
tgaatccagt gaatacccac tgttaatatt tggtatatct cttctagtc ttttttttccc     17820 ttttgcatgt attttctta agactccac ccccactgga tcatctctgc atgttctaat    17880 ctgcttttt cacagcagat tctaagcctc tttgaatatc aacacaaact tcaacaactt    17940
catctataga tgccaaataa taattcatt tttatttact taaccacttc ctttggatgc    18000
ttaggtcatt ctgatgtttt gctattgaaa ccaatgctat actgaacact tctgtcacta    18060
aaactttgca cacactcatg aatagcttct taggataaat ttttagagat ggatttgcta    18120
```

```
aatcagagac catttttaa aattaaaaaa caattattca tatcgtttgg catgtaagac    18180
agtaaatttt cctttattt tgacaggatt caactggaag ctttgtgctg cctttccggc    18240
aagtcatgta tgctccatat cccaccacac acatagatgt ggatgtcaat actgtgaagc    18300
agatgccacc ctgtcatgaa catatttata atcagcgtag atacatgaga tccgagctga    18360
cagccttctg gagagccact tcagaagaag acatggctca ggatacgatc atctacactg    18420
acgaaagctt tactcctgat ttgtacgtaa tgctctgcct gctggtactg tagtcaagca    18480
atatgaaatt gtgtctttta cgaataaaaa caaaacagaa gttgcattta aaagaaaga    18540 aatattacca gcagaattat gcttgaagaa acatttaatc aagcatttt tcttaaatg     18600 ttcttctttt tccatacaat tgtgtttacc ctaaatagg taagattaac ccttaaagta    18660
aatatttaac tatttgttta ataaatatat attgagctcc taggcactgt tctaggtacc    18720
gggcttaata gtggccaacc agacagcccc agcccagcc cctacattgt gtatagtcta    18780
ttatgtaaca gttattgaat ggacttatta acaaaaccaa agaagtaatt ctaagtcttt    18840
tttttcttga catatgaata taaaatacag caaaactgtt aaaatatatt aatggaacat    18900 tttttactt tgcattttat attgttattc acttcttatt tttttttaaa aaaaaagcc     18960 tgaacagtaa attcaaaagg aaaagtaatg ataattaatt gttgagcatg gacccaactt    19020
gaaaaaaaaa atgatgatga taaatctata atcctaaaac cctaagtaaa cacttaaaag    19080
atgttctgaa atcaggaaaa gaattatagt atactttgt gtttctcttt tatcagttga    19140
aaaaaggcac agtagctcat gcctgtaaga acagagcttt gggagtgcaa ggcaggcgga    19200
tcacttgagg ccaggagttc cagaccagcc tgggcaacat agtgaaaccc catctctaca    19260
aaaaataaaa aagaattatt ggaatgtgtt tctgtgtgcc tgtaatccta gctattccga    19320
aagctgaggc aggaggatct tttgagccca ggagtttgag gttacaggga gttatgatgt    19380
gccagtgtac tccagcctgg ggaacaccga gactctgtct tatttaaaaa aaaaaaaaa    19440 aaaatgcttg caataatgcc tggcacatag aaggtaacag taagtgttaa ctgtaataac    19500
ccaggtctaa gtgtgtaagg caatagaaaa attggggcaa ataagcctga cctatgtatc    19560
tacagaatca gtttgagctt aggtaacaga cctgtggagc accagtaatt acacagtaag    19620
tgttaaccaa aagcatagaa taggaatatc ttgttcaagg acccccagc cttatacatc     19680 tcaaggtgca gaaagatgac ttaatatagg acccattttt tcctagttct ccagagtttt    19740
tattggttct tgagaaagta gtaggggaat gttttagaaa atgaattggt ccaactgaaa    19800
ttacatgtca gtaagttttt atatattggt aaatttagt agacatgtag aagttttcta    19860
attaatctgt gccttgaaac attttctttt ttcctaaagt gcttagtatt ttttccgttt    19920
tttgattggt tacttgggag cttttttgag gaaatttagt gaactgcaga atgggtttgc    19980
aaccatttgg tatttttgtt ttgttttta gaggatgtat gtgtatttta acatttctta    20040 atcatttta gccagctatg tttgtttgc tgatttgaca aactacagtt agacagctat      20100
tctcattttg ctgatcatga caaataata tcctgaattt ttaaattttg catccagctc    20160
taaattttct aaacataaaa ttgtccaaaa aatagtattt tcagccacta gattgtgtgt    20220
taagtctatt gtcacagagt catttttactt ttaagtatat gttttacat gttaattatg    20280 tttgttattt ttaattttaa cttttaaaa taattccagt cactgccaat acatgaaaaa    20340
ttggtcactg gaattttttt tttgactttt attttaggtt catgtgtaca tgtgcaggtg    20400
tgttatacag gtaaattgcg tgtcatgagg gtttggtgta caggtgattt cattacccag    20460
```

```
gtaataagca tagtacccaa taggtagttt tttgatcctc acccttctcc caccctcaag    20520
taggccctgg tgttgctgtt tccttctttg tgtccatgta tactcagtgt ttagctccca    20580
cttagaagtg agaacatgcg gtagttggtt ttctgttcct ggattagttc acttaggata    20640
atgacctcta gctccatctg gttttttatgg ctgcatagta ttccatggtg tatatgtatc    20700
acatttcctt tatccagtct accattgata ggcatttagg ttgattccct gtctttgtta    20760
tcatgaatag tgctgtgatg aacatacaca tgcatgtgtc tttatggtag aaaaatttgt    20820
attcctttag gtacatatag aataatgggg ttgctagggt gaatggtagt tctattttca    20880
gttatttgag aaatcttcaa actgcttttc ataatagcta aactaattta cagtcccgcc    20940
agcagtgtat aagtgttccc ttttctccac aaccttgcca acatctgtga tttttttgact   21000
ttttaataat agccattcct agagaattga tttgcaattc tctattagtg atattaagca    21060
ttttttcata tgcttttag ctgtctgtat atattcttct gaaaaatttt catgtccttt     21120
gcccagtttg tagtggggtg ggttgttttt tgcttgttaa ttagttttaa gttccttcca    21180
gattctgcat atccctttgt tggatacatg gtttgcagat attttctcc cattgtgtag     21240
gttgtctttt actctgttga tagtttcttt tgccatgcag gagctcgtta ggtcccattt    21300
gtgtttgttt ttgttgcagt tgcttttggc gtcttcatca taaaatctgt gccagggcct    21360
atgtccagaa tggtatttcc taggttgtct tccaggggtt ttacaatttt agattttacg    21420
tttatgtctt taatccatct tgagttgatt tttgtatatg gcacaaggaa ggggtccagt    21480
ttcactccaa ttcctatggc tagcaattat cccagcacca tttattgaat acggagtcct    21540
ttccccattg cttgttttttt gtcaactttg ttgaagatca gatggttgta agtgtgtggc   21600
tttatttctt ggctctctat tctccattgg tctatgtgtc tgttttttata acagtaccct    21660
gctgttcagg ttcctatagc cttttagtat aaaatcggct aatgtgatgc ctccagcttt    21720
gttcttttttg cttaggattg ctttggctat ttgggctcct ttttgggtcc atattaattt    21780
taaaacagtt ttttctggtt ttgtgaagga tatcattggt agtttatagg aatagcattg    21840
aatctgtaga ttgctttggg cagtatggcc attttaacaa tattaattct tcctatctat    21900
gaatatggaa tgttttttcca tgtgtttgtg tcatctcttt tacctgatg tataaagaaa    21960
agctggtatt attcctactc aatctgttcc aaaaaattga ggaggaggaa ctcttcccta    22020
atgaggccag catcattctg ataccaaaac ctggcagaga cacaacgaaa aaagaaaac    22080
ttcaggccaa tatccttgat gaatatagat gcaaaaatcc tcaacaaaat actagcaaac    22140
caaatccagc agcacatcaa aaagctgatc tactttgatc aagtaggctt tatccctggg    22200
atgcaaggtt ggttcaacat acacaaatca ataagtgtga ttcatcacat aaacagagct    22260
aaaaacaaaa accacaagat tatctcaata ggtagagaaa aggttgtcaa taaaatttaa    22320
catcctccat gttaaaaacc ttcagtaggt caggtgtagt gactcacacc tgtaatccca    22380
gcactttggg aggccaaggc gggcatatct cttaagccca ggagttcaag acgagcctag    22440
gcagcatggt gaaaccccat ctctacaaaa aaaaaaaaa aaaaaaatta gcttggtatg    22500
gtgacatgca cctatagtcc cagctattca ggaggttgag gtgggaggat tgtttgagcc    22560
cgggaggcag aggttggcag cgagctgaga tcatgccacc gcactccagc ctgggcaacg    22620
gagtgagacc ctgtctcaaa aagaaaaat cacaaacaat cctaaacaaa ctaggcattg     22680
aaggaacatg cctcaaaaaa ataagaacca tctatgacag acccatagcc aatatcttac    22740
caaatgggca aaagctggaa gtattctcct tgagaaccgt aacaagacaa ggatgtccac    22800
tctcaccact cctttcagc atagttctgg aagtcctagc cagagcaatc aggaaagaga    22860
```

| | |
|---|---|
| aagaaagaaa gacattcaga taggaagaga agaagtcaaa ctatttctgt ttgcaggcag | 22920 |
| tataattctg tacctagaaa atctcatagt ctctgcccag aaactcctaa atctgttaaa | 22980 |
| aatttcagca aagttttggc attctctata ctccaacacc ttccaaagtg agagcaaaat | 23040 |
| caagaacaca gtcccattca caatagccgc aaaacgaata aaatacctag gaatccagct | 23100 |
| aaccagggag gtgaaagatc tctatgagaa ttacaaaaca ctgctgaaag aaatcagaga | 23160 |
| tgacacaaac aaatggaaat gttcttttt aacaccttgc tttatctaat tcacttatga | 23220 |
| tgaagatact cattcagtgg aacaggtata ataagtccac tcgattaaat ataagcctta | 23280 |
| ttctcttcc agagcccaag aaggggcact atcagtgccc agtcaataat gacgaaatgc | 23340 |
| taatattttt cccctttacg gtttctttct tctgtagtgt ggtacactcg tttcttaaga | 23400 |
| taaggaaact tgaactacct tcctgtttgc ttctacacat acccattctc ttttttgcc | 23460 |
| actctggtca ggtataggat gatccctacc actttcagtt aaaaactcct cctcttacta | 23520 |
| aatgttctct taccctctgg cctgagtaga acctagggaa aatggaagag aaaaagatga | 23580 |
| aagggaggtg gggcctggga agggaataag tagtcctgtt tgtttgtgtg tttgctttag | 23640 |
| cacctgctat atcctaggtg ctgtgttagg cacacattat tttaagtggc cattatatta | 23700 |
| ctactactca ctctggtcgt tgccaaggta ggtagtactt tcttggatag ttggttcatg | 23760 |
| ttacttacag atggtgggct tgttgaggca aacccagtgg ataatcatcg gagtgtgttc | 23820 |
| tctaatctca ctcaaatttt tcttcacatt ttttggtttg ttttggtttt tgatggtagt | 23880 |
| ggcttatttt tgttgctggt ttgttttttg ttttttttg agatggcaag aattggtagt | 23940 |
| tttatttatt aattgcctaa gggtctctac ttttttaaa agatgagagt agtaaaatag | 24000 |
| attgatagat acatcatac ccttactggg gactgcttat attctttaga gaaaaaatta | 24060 |
| catattagcc tgacaaacac cagtaaaatg taaatatatc cttgagtaaa taaatgaatg | 24120 |
| tatattttgt gtctccaaat atatatatct atattcttac aaatgtgttt atatgtaata | 24180 |
| tcaatttata agaacttaaa atgttggctc aagtgaggga ttgtggaagg tagcattata | 24240 |
| tggccatttc aacatttgaa cttttttctt ttcttcattt tcttctttc ttcaggaata | 24300 |
| tttttcaaga tgtcttacac agagacactc tagtgaaagc cttcctggat caggtaaatg | 24360 |
| ttgaacttga gattgtcaga gtgaatgata tgacatgttt tcttttttaa tatatcctac | 24420 |
| aatgcctgtt ctatatattt atattcccct ggatcatgcc ccagagttct gctcagcaat | 24480 |
| tgcagttaag ttagttacac tacagttctc agaagagtct gtgagggcat gtcaagtgca | 24540 |
| tcattacatt ggttgcctct tgtcctagat ttatgcttcg ggaattcaga cctttgttta | 24600 |
| caatataata aatattattg ctatcttta aagatataat aataagatat aaagttgacc | 24660 |
| acaactactg ttttttgaaa catagaattc ctggtttaca tgtatcaaag tgaaatctga | 24720 |
| cttagctttt acagatataa tatatacata tatatatcct gcaatgcttg tactatatat | 24780 |
| gtagtacaag tatatatata tgtttgtgtg tgtatatata tatagtacga gcatatatac | 24840 |
| atattaccag cattgtagga tatatatatg tttatatatt aaaaaaaagt tataaactta | 24900 |
| aaaccctatt atgttatgta gagtatatgt tatatatgat atgtaaaata tataacatat | 24960 |
| actctatgat agagtgtaat atattttta tatatttt aacatttata aaatgataga | 25020 |
| attaagaatt gagtcctaat ctgtttatt aggtgctttt tgtagtgtct ggtctttcta | 25080 |
| aagtgtctaa atgattttc cttttgactt attaatgggg aagagcctgt atattaacaa | 25140 |
| ttaagagtgc agcattccat acgtcaaaca acaaacattt taattcaagc attaacctat | 25200 |

```
aacaagtaag ttttttttt ttttttgaga aagggaggtt gtttatttgc ctgaaatgac    25260
tcaaaaatat ttttgaaaca tagtgtactt atttaaataa catctttatt gtttcattct    25320
tttaaaaaat atctacttaa ttacacagtt gaaggaaatc gtagattata tggaacttat    25380
ttcttaatat attacagttt gttataataa cattctgggg atcaggccag gaaactgtgt    25440
catagataaa gctttgaaat aatgagatcc ttatgtttac tagaaatttt ggattgagat    25500
ctatgaggtc tgtgacatat tgcgaagttc aaggaaaatt cgtaggcctg gaatttcatg    25560
cttctcaagc tgacataaaa tccctcccac tctccacctc atcatatgca cacattctac    25620
tcctacccac ccactccacc ccctgcaaaa gtacaggtat atgaatgtct caaaaccata    25680
ggctcatctt ctaggagctt caatgttatt tgaagatttg ggcagaaaaa attaagtaat    25740
acgaaataac ttatgtatga gttttaaaag tgaagtaaac atggatgtat tctgaagtag    25800
aatgcaaaat ttgaatgcat ttttaaagat aaattagaaa acttctaaaa actgtcagat    25860
tgtctgggcc tggtggctta tgcctgtaat cccagcactt tgggagtccg aggtgggtgg    25920
atcacaaggt caggagatcg agaccatcct gccaacatgg tgaaaccccg tctctactaa    25980
gtatacaaaa attagctggg cgtggcagcg tgtgcctgta atcccagcta cctgggaggc    26040
tgaggcagga gaatcgcttg aacccaggag gtgtaggttg cagtgagtca agatcgcgcc    26100
actgcacttt agcctggtga cagagctaga ctccgtctca aaaaaaaaaa aaaatatcag    26160
attgttccta cacctagtgc ttctatacca cactcctgtt aggggcatc agtggaaatg     26220 gttaaggaga tgtttagtgt gtattgtctg ccaagcactg tcaacactgt catagaaact    26280
tctgtacgag tagaatgtga gcaaattatg tgttgaaatg gttcctctcc ctgcaggtct    26340
ttcagctgaa acctggctta tctctcagaa gtactttcct tgcacagttt ctacttgtcc    26400
ttcacagaaa agccttgaca ctaataaaat atatagaaga cgatacgtga gtaaaactcc    26460
tacacggaag aaaaaccttt gtacattgtt tttttgtttt gtttcctttg tacatttttct   26520 atatcataat ttttgcgctt cttttttttt tttttttttt tttttttcca ttattttag    26580 gcagaaggga aaaagcccct ttaaatctct tcggaacctg aagatagacc ttgatttaac    26640
agcagagggc gatcttaaca taataatggc tctggctgag aaaattaaac caggcctaca    26700
ctcttttatc tttggaagac cttttctacac tagtgtgcaa gaacgagatg ttctaatgac    26760
tttttaaatg tgtaacttaa taagcctatt ccatcacaat catgatcgct ggtaaagtag    26820
ctcagtggtg tggggaaacg ttcccctgga tcatactcca gaattctgct ctcagcaatt    26880
gcagttaagt aagttacact acagttctca caagagcctg tgagggatg tcaggtgcat     26940 cattacattg ggtgtctctt ttcctagatt tatgcttttg ggatacagac ctatgtttac    27000
aatataataa atattattgc tatctttta agatataata ataggatgta aacttgacca    27060
caactactgt tttttgaaa tacatgattc atggtttaca tgtgtcaagg tgaaatctga    27120
gttggctttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
attggaattg attattagat cctactttgt ggatttagtc cctgggattc agtctgtaga    27360
aatgtctaat agttctctat agtccttgtt cctggtgaac cacagttagg gtgttttgtt    27420
tattttattg ttcttgctat tgttgatatt ctatgtagtt gagctctgta aaaggaaatt    27480
gtattttatg ttttagtaat tgttgccaac ttttaaatt aatttttcatt attttttgagc   27540 caaattgaaa tgtgcaccctc ctgtgccttt tttctcctta gaaaatctaa ttacttggaa    27600
```

```
caagttcaga tttcactggt cagtcatttt catcttgttt tcttcttgct aagtcttacc   27660
atgtacctgc tttggcaatc attgcaactc tgagattata aaatgcctta gagaatatac   27720
taactaataa gatctttttt tcagaaacag aaaatagttc cttgagtact tccttcttgc   27780
atttctgcct atgtttttga agttgttgct gtttgcctgc aataggctat aaggaatagc   27840
aggagaaatt ttactgaagt gctgttttcc taggtgctac tttggcagag ctaagttatc   27900
ttttgttttc ttaatgcgtt tggaccattt tgctggctat aaaataactg attaatataa   27960
ttctaacaca atgttgacat tgtagttaca caaacacaaa taaatatttt atttaaaatt   28020
ctggaagtaa tataaaaggg aaaatatatt tataagaaag ggataaaggt aatagagccc   28080
ttctgccccc cacccaccaa atttacacaa caaaatgaca tgttcgaatg tgaaaggtca   28140
taatagcttt cccatcatga atcagaaaga tgtggacagc ttgatgtttt agacaaccac   28200
tgaactagat gactgttgta ctgtagctca gtcatttaaa aaatatataa atactacctt   28260
gtagtgtccc atactgtgtt ttttacatgg tagattctta tttaagtgct aactggttat   28320
tttctttggc tggtttattg tactgttata cagaatgtaa gttgtacagt gaaataagtt   28380
attaaagcat gtgtaaacat tgttatatat cttttctcct aaatggagaa ttttgaataa   28440
aatatatttg aaattttgcc tctttcagtt gttcattcag aaaaaaatac tatgatattt   28500
gaagactgat cagcttctgt tcagctgaca gtcatgctgg atctaaactt tttttaaaat   28560
taattttgtc ttttcaaaga aaaatatttt aaagaagctt tataatataa tcttatgtta   28620
aaaaaacttt ctgcttaact ctctggattt cattttgatt tttcaaatta tatattaata   28680
tttcaaatgt aaaatactat ttagataaat tgttttttaaa cattcttatt attataatat   28740
taatataacc taaactgaag ttattcatcc caggtatcta atacatgtat ccaaagtaaa   28800
aatccaagga atctgaacac tttcatctgc aaagctagga ataggtttga cattttcact   28860
ccaagaaaaa gtttttttttt gaaaatagaa tagttgggat gagaggtttc tttaaaagaa   28920
gactaactga tcacattact atgattctca aagaagaaac caaaacttca tataatacta   28980
taaagtaaat ataaaatagt tccttctata gtatatttct ataatgctac agtttaaaca   29040
gatcactctt atataatact attttgattt tgatgtgaaa ttgcacaaat tgatatttct   29100
cctatgatct gcagggtata gcttaaagta acaaaaacag tcaaccacct ccatttaaca   29160
cacagtaaca ctatgggact agtttttatta cttccatttt acaaatgagg aaactaaagc   29220
ttaaagatgt gtaatacacc gcccaaggtc acacagctgg taaaggtgga tttcatccca   29280
gacagttaca gtcattgcca tgggcacagc tcctaactta gtaactccat gtaactggta   29340
ctcagtgtag ctgaattgaa aggagagtaa ggaagcaggt tttacaggtc tacttgcact   29400
attcagagcc cgagtgtgaa tccctgctgt gctgcttgga gaagttactt aacctatgca   29460
aggttcattt tgtaaatatt ggaaatggag tgataatacg tacttcacca gaggatttaa   29520 tgagaccttta tacgatcctt agttcagtac ctgactagtg cttcataaat gcttttttcat   29580 ccaatctgac aatctccagc ttgtaattgg ggcatttaga acatttaata tgattattgg   29640
catggtaggt taaagctgtc atcttgctgt tttctatttg ttcttttttgt tttctcctta   29700 cttttggatt ttttttattct actatgtctt ttctattgtc ttattaacta tactctttga   29760
tttattttag tggttgtttt agggttatac ctctttctaa tttaccagtt tataaccagt   29820
ttatatacta cttgacatat agcttaagaa acttactgtt gttgtctttt tgctgttatg   29880
gtcttaacgt ttttatttct acaaacatta taaactccac actttattgt tttttaattt   29940
```

| | |
|---|---|
| tacttataca gtcaattatc tttttaaagat atttaaatat aaacattcaa aacacccccaa | 30000 |
| t | 30001 |

<210> SEQ ID NO 3
<211> LENGTH: 1031
<212> TYPE: DNA
<213> ORGANISM: Homo sapiens

<400> SEQUENCE: 3

| | |
|---|---|
| attcccggga tacgtaacct acggtgtccc gctaggaaag agaggtgcgt caaacagcga | 60 |
| caagttccgc ccacgtaaaa gatgacgctt ggtgtgtcag ccgtccctgc tgcccggttg | 120 |
| cttctctttt gggggcgggg tctagcaaga gcaggtgtgg gtttaggaga tatctccgga | 180 |
| gcatttggat aatgtgacag ttggaatgca gtgatgtcga ctctttgccc accgccatct | 240 |
| ccagctgttg ccaagacaga gattgcttta agtggcaaat cacctttatt agcagctact | 300 |
| tttgcttact gggacaatat tcttggtcct agagtaaggc acatttgggc tccaaagaca | 360 |
| gaacaggtac ttctcagtga tggagaaata acttttcttg ccaaccacac tctaaatgga | 420 |
| gaaatccttc gaaatgcaga gagtggtgct atagatgtaa agttttttgt cttgtctgaa | 480 |
| aagggagtga ttattgtttc attaatcttt gatggaaact ggaatgggga tcgcagcaca | 540 |
| tatggactat caattatact tccacagaca gaacttagtt tctacctccc acttcataga | 600 |
| gtgtgtgttg atagattaac acatataatc cggaaaggaa gaatatggat gcataaggaa | 660 |
| agacaagaaa atgtccaga agattatctt agaaggcaca gagagaatgg aagatcaggg | 720 |
| tcagagtatt attccaatgc ttactggaga agtgattcct gtaatggaaa ctgctttcct | 780 |
| ctatgaaatt cccccgggtt cctggaggaa atagatatag gctgatacag ttacccaatg | 840 |
| atggatgaat attgggggac cgcctggtca ttgaaaggct ttcttttctc caggaaagaa | 900 |
| atttttttcc ttttccataa aaagcttggg aatggaagac aacaattccc attctttttt | 960 |
| tgcgttccac ccctatgtga caacagaaat ttttggggaa acaacaacga aaaaatttta | 1020 |
| tcccgcgcgc a | 1031 |

<210> SEQ ID NO 4
<211> LENGTH: 3244
<212> TYPE: DNA
<213> ORGANISM: Homo sapiens

<400> SEQUENCE: 4

| | |
|---|---|
| gggcggggct gcggttgcgg tgcctgcgcc cgcggcggcg gaggcgcagg cggtggcgag | 60 |
| tggatatctc cggagcattt ggataatgtg acagttggaa tgcagtgatg tcgactctt | 120 |
| gcccaccgcc atctccagct gttgccaaga cagagattgc tttaagtggc aaatcacctt | 180 |
| tattagcagc tactttttgct tactgggaca atattcttgg tcctagagta aggcacattt | 240 |
| gggctccaaa gacagaacag gtacttctca gtgatggaga ataacttttt cttgccaacc | 300 |
| acactctaaa tggagaaatc cttcgaaatg cagagagtgg tgctatagat gtaaagtttt | 360 |
| ttgtcttgtc tgaaaaggga gtgattattg tttcattaat ctttgatgga aactggaatg | 420 |
| gggatcgcag cacatatgga ctatcaatta tacttccaca gacagaactt agttctacc | 480 |
| tcccacttca tagagtgtgt gttgatagat taacacatat aatccggaaa ggaagaatat | 540 |
| ggatgcataa ggaaagacaa gaaaatgtcc agaagattat cttagaaggc acagagagaa | 600 |
| tggaagatca gggtcagagt attattccaa tgcttactgg agaagtgatt cctgtaatgg | 660 |
| aactgctttc atctatgaaa tcacacagtg ttcctgaaga aatagatata gctgatacag | 720 |

```
tactcaatga tgatgatatt ggtgacagct gtcatgaagg ctttcttctc aatgccatca    780
gctcacactt gcaaacctgt ggctgttccg ttgtagtagg tagcagtgca gagaaagtaa    840
ataagatagt cagaacatta tgcctttttc tgactccagc agagagaaaa tgctccaggt    900
tatgtgaagc agaatcatca tttaaatatg agtcagggct ctttgtacaa ggcctgctaa    960
aggattcaac tggaagcttt gtgctgcctt tccggcaagt catgtatgct ccatatccca   1020
ccacacacat agatgtggat gtcaatactg tgaagcagat gccaccctgt catgaacata   1080
tttataatca gcgtagatac atgagatccg agctgacagc cttctggaga gccacttcag   1140
aagaagacat ggctcaggat acgatcatct acactgacga aagctttact cctgatttga   1200 atattttca agatgtctta cacagagaca ctctagtgaa agccttcctg gatcaggtct   1260
ttcagctgaa acctggctta tctctcagaa gtactttcct tgcacagttt ctacttgtcc   1320
ttcacagaaa agccttgaca ctaataaaat atatagaaga cgatacgcag aagggaaaaa   1380 agcccttaa atctcttcgg aacctgaaga tagaccttga tttaacagca gagggcgatc   1440
ttaacataat aatggctctg gctgagaaaa ttaaaccagg cctacactct tttatctttg   1500
gaagaccttt ctacactagt gtgcaagaac gagatgttct aatgactttt taaatgtgta   1560
acttaataag cctattccat cacaatcatg atcgctggta aagtagctca gtggtgtggg   1620
gaaacgttcc cctggatcat actccagaat tctgctctca gcaattgcag ttaagtaagt   1680
tacactacag ttctcacaag agcctgtgag gggatgtcag gtgcatcatt acattgggtg   1740
tctcttttcc tagatttatg cttttgggat acagacctat gtttacaata taataaatat   1800
tattgctatc ttttaaagat ataataatag gatgtaaact tgaccacaac tactgttttt   1860
ttgaaataca tgattcatgg tttacatgtg tcaaggtgaa atctgagttg gcttttacag   1920
atagttgact ttctatcttt tggcattctt tggtgtgtag aattactgta atacttctgc   1980
aatcaactga aaactagagc ctttaaatga tttcaattcc acagaaagaa agtgagcttg   2040
aacataggat gagctttaga aagaaaattg atcaagcaga tgtttaattg gaattgatta   2100
ttagatccta ctttgtggat ttagtccctg ggattcagtc tgtagaaatg tctaatagtt   2160
ctctatagtc cttgttcctg gtgaaccaca gttagggtgt tttgtttatt ttattgttct   2220
tgctattgtt gatattctat gtagttgagc tctgtaaaag gaaattgtat tttatgtttt   2280
agtaattgtt gccaactttt taaattaatt ttcattattt ttgagccaaa ttgaaatgtg   2340
cacctcctgt gcctttttc tccttagaaa atctaattac ttggaacaag ttcagatttc   2400
actggtcagt cattttcatc ttgttttctt cttgctaagt cttaccatgt acctgctttg   2460
gcaatcattg caactctgag attataaaat gccttagaga atatactaac taataagatc   2520 ttttttcag aaacagaaaa tagttccttg agtacttcct tcttgcattt ctgcctatgt   2580
ttttgaagtt gttgctgttt gcctgcaata ggctataagg aatagcagga gaaattttac   2640
tgaagtgctg ttttcctagg tgctactttg gcagagctaa gttatctttt gttttcttaa   2700
tgcgtttgga ccattttgct ggctataaaa taactgatta atataattct aacacaatgt   2760
tgacattgta gttacacaaa cacaaataaa tattttattt aaaattctgg aagtaatata   2820
aaagggaaaa tatatttata agaaagggat aaaggtaata gagcccttct gcccccacc   2880 caccaaattt acacaacaaa atgacatgtt cgaatgtgaa aggtcataat agctttccca   2940
tcatgaatca gaaagatgtg gacagcttga tgttttagac aaccactgaa ctagatgact   3000
gttgtactgt agctcagtca tttaaaaaat atataaatac taccttgtag tgtcccatac   3060
```

| | |
|---|---|
| tgtgtttttt acatggtaga ttcttattta agtgctaact ggttatttc tttggctggt | 3120 |
| ttattgtact gttatacaga atgtaagttg tacagtgaaa taagttatta aagcatgtgt | 3180 |
| aaacattgtt atatatcttt tctcctaaat ggagaatttt gaataaaata tatttgaaat | 3240 |
| tttg | 3244 |

```
<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5
```

| | |
|---|---|
| cacgaggctt tgatatttct tacaacgaat tcatgtgta gacccactaa acagaagcta | 60 |
| taaaagttgc atggtcaaat aagtctgaga agtctgcag atgatataat tcacctgaag | 120 |
| agtcacagta tgtagccaaa tgttaaaggt tttgagatgc catacagtaa atttaccaag | 180 |
| cattttctaa atttatttga ccacagaatc ctatttaa gcaacaactg ttacatccca | 240 |
| tggattccag gtgactaaag aatacttatt tcttaggata tgttttattg ataataacaa | 300 |
| ttaaaatttc agatatcttt cataagcaaa tcagtggtct ttttacttca tgttttaatg | 360 |
| ctaaaatatt ttcttttata gatagtcaga acattatgcc ttttctgac tccagcagag | 420 |
| agaaaatgct ccaggttatg tgaagcagaa tcatcattta aatatgagtc agggctcttt | 480 |
| gtacaaggcc tgctaaagga ttcaactgga agctttgtgc tgccttccg gcaagtcatg | 540 |
| tatgctccat atcccaccac acacatagat gtggatgtca atactgtgaa gcagatgcca | 600 |
| ccctgtcatg aacatattta taatcagcgt agatacatga gatccgagct gacagccttc | 660 |
| tggagagcca cttcagaaga agacatggct cangatacga tcatctacac tgacgaaagc | 720 |
| tntactcctg atttgaatat ttttcaagat gtcttacaca g | 761 |

```
<210> SEQ ID NO 6
<211> LENGTH: 1901
<212> TYPE: DNA
<213> ORGANISM: Homo sapiens

<400> SEQUENCE: 6
```

| | |
|---|---|
| acgtaaccta cggtgtcccg ctaggaaaga gaggtgcgtc aaacagcgac aagttccgcc | 60 |
| cacgtaaaag atgacgcttg atatctccgg agcatttgga taatgtgaca gttggaatgc | 120 |
| agtgatgtcg actctttgcc caccgccatc tccagctgtt gccaagacag agattgcttt | 180 |
| aagtggcaaa tcacctttat tagcagctac ttttgcttac tgggacaata ttcttggtcc | 240 |
| tagagtaagg cacatttggg ctccaaagac agaacaggta cttctcagtg atggagaaat | 300 |
| aacttttctt gccaaccaca ctctaaatgg agaaatcctt cgaaatgcag agagtggtgc | 360 |
| tatagatgta aagttttttg tcttgtctga aaagggagtg attattgttt cattaatctt | 420 |
| tgatggaaac tggaatgggg atcgcagcac atatggacta tcaattatac ttccacagac | 480 |
| agaacttagt ttctacctcc cacttcatag agtgtgtgtt gatagattaa cacatataat | 540 |
| ccggaaagga agaatatgga tgcataagga aagacaagaa aatgtccaga agattatctt | 600 |
| agaaggcaca gagagaatgg aagatcaggg tcagagtatt attccaatgc ttactggaga | 660 |

-continued

```
agtgattcct gtaatggaac tgctttcatc tatgaaatca cacagtgttc ctgaagaaat      720
agatatagct gatacagtac tcaatgatga tgatattggt gacagctgtc atgaaggctt      780
tcttctcaag taagaatttt tcttttcata aaagctggat gaagcagata ccatcttatg      840
ctcacctatg acaagatttg gaagaaagaa ataacagac tgtctactta gattgttcta       900
gggacattac gtatttgaac tgttgcttaa atttgtgtta tttttcactc attatatttc      960
tatatatatt tggtgttatt ccatttgcta tttaaagaaa ccgagtttcc atcccagaca     1020
agaaatcatg gccccttgct tgattctggt ttcttgtttt acttctcatt aaagctaaca     1080 gaatccttc atattaagtt gtactgtaga tgaacttaag ttatttaggc gtagaacaaa      1140
attattcata tttatactga tcttttccca tccagcagtg gagtttagta cttaagagtt     1200 tgtgcccta aaccagactc cctggattaa tgctgtgtac ccgtgggcaa ggtgcctgaa      1260
ttctctatac acctatttcc tcatctgtaa aatggcaata atagtaatag tacctaatgt     1320
gtagggttgt tataagcatt gagtaagata aataatataa agcacttaga acagtgcctg     1380
gaacataaaa acacttaata atagctcata gctaacattt cctatttaca tttcttctag     1440
aaatagccag tatttgttga gtgcctacat gttagttcct ttactagttg ctttacatgt     1500
attatcttat attctgtttt aaagtttctt cacagttaca gattttcatg aaattttact     1560
tttaataaaa gagaagtaaa agtataaagt attcactttt atgttcacag tcttttcctt     1620
taggctcatg atggagtatc agaggcatga gtgtgtttaa cctaagagcc ttaatggctt     1680
gaatcagaag cactttagtc ctgtatctgt tcagtgtcag cctttcatac atcattttaa     1740
atcccatttg actttaagta agtcacttaa tctctctaca tgtcaatttc ttcagctata     1800
aaatgatggt atttcaataa ataaatacat taattaaatg atattatact gactaattgg     1860
gctgttttaa ggcaaaaaaa aaaaaaaaaa aaaaaaaaa a                           1901
```

<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

```
agacgtaacc tacggtgtcc cgctaggaaa gagagatatc tccggagcat tggataatg       60 tgacagttgg aatgcagtga tgtcgactct ttgcccaccg ccatctccag ctgttgccaa     120
gacagagatt gctttaagtg gcaaatcacc tttattagca gctacntttt gcttactggg     180
acaatattct tggtcctaga gtaaggcaca tttgggctcc aaagacagaa caggtacttc     240
tcagtgatgg agaaataact tttcttgcca accacactct aaatggagaa atccttcgaa     300
atgcagagag tggtgctata gatgtaaagt ttttgtctt gtctgaaaag ggagtgatta      360
ttgtttcatt aatctttgat ggaaactgga atggggatcg cagcacatat ggactatcaa     420
ttatacttcc acagacagaa cttagtttct acctcccact tcatagagtg tgtgttgata     480
gattaacaca tataatccgg aaaggaagaa tatggatgca taggaaaga caagaaaatg      540 tccagaagat tatcttagaa gg                                              562
```

<210> SEQ ID NO 8
<211> LENGTH: 798
<212> TYPE: DNA

<213> ORGANISM: Homo sapiens

<400> SEQUENCE: 8

| gggctctctt | ttgggggcgg | ggtctagcaa | gagcagatat | ctccggagca | tttggataat | 60 |
| gtgacagttg | gaatgcagtg | atgtcgactc | tttgcccacc | gccatctcca | gctgttgcca | 120 |
| agacagagat | tgctttaagt | ggcaaatcac | ctttattagc | agctactttt | gcttactggg | 180 |
| acaatattct | tggtcctaga | gtaaggcaca | tttgggctcc | aaagacagaa | caggtacttc | 240 |
| tcagtgatgg | agaaataact | tttcttgcca | accacactct | aaatggagaa | atccttcgaa | 300 |
| atgcagagag | tggtgctata | gatgtaaagt | tttttgtctt | gtctgaaaag | ggagtgatta | 360 |
| ttgtttcatt | aatctttgat | ggaaactgga | atggggatcg | cagcacatat | ggactatcaa | 420 |
| ttatacttcc | acagacagaa | cttagtttct | acctcccact | tcatagagtg | tgtgttgata | 480 |
| gattaacaca | tataatccgg | aaaggaagaa | tatggatgca | taaggaaaga | caagaaaatg | 540 |
| tccagaagat | tatcttagaa | ggcacagaga | gaatggaaga | tcagggtcag | agtattattc | 600 |
| caatgcttac | tggagaagtg | attcctgtaa | tgggactgct | tcatctatg | aaatcacaca | 660 |
| gtgttcctga | agaaatagat | atagctgata | cagtactcca | tgatgatgat | atttggtgac | 720 |
| agctgtcatg | aaaggctttc | ttctcaagta | ggaattttt | ctttcataa | aagctgggat | 780 |
| gaagccagat | tcccatct | | | | | 798 |

<210> SEQ ID NO 9
<211> LENGTH: 169
<212> TYPE: DNA
<213> ORGANISM: Homo sapiens

<400> SEQUENCE: 9

| aaacagcgac | aagttccgcc | cacgtaaaag | atgatgcttg | gtgtgtcagc | cgtccctgct | 60 |
| gcccggttgc | ttctcttttg | ggggcggggt | ctagcaagag | cagatatctc | cggagcattt | 120 |
| ggataatgtg | acagttggaa | tgcggtgatg | tcgactcttt | gcccaccgc | | 169 |

<210> SEQ ID NO 10
<211> LENGTH: 176
<212> TYPE: DNA
<213> ORGANISM: Homo sapiens

<400> SEQUENCE: 10

| aaaacgtcat | cgcacataga | aaacagacag | acgtaaccta | cggtgtcccg | ctaggaaaga | 60 |
| gaggtgcgtc | aaacagcgac | aagttccgcc | cacgtaaaag | atgacgcttg | atatctccgg | 120 |
| agcatttgga | taatgtgaca | gttggaatgc | agtgatgtcg | actctttgcc | caccgc | 176 |

<210> SEQ ID NO 11

<400> SEQUENCE: 11

000

<210> SEQ ID NO 12

<400> SEQUENCE: 12

000

<210> SEQ ID NO 13
<211> LENGTH: 783
<212> TYPE: DNA
<213> ORGANISM: Homo sapiens

<400> SEQUENCE: 13

```
gcctctcagt acccgaggct ccctttctc gagcccgcag cggcagcgct cccagcgggt      60
ccccgggaag gagacagctc gggtactgag ggcgggaaag caaggaagag gccagatccc     120
catcccttgt ccctgcgccg ccgccgccgc cgccgccgcc gggaagcccg ggccccggat    180
gcaggcaatt ccaccagtcg ctagaggcga aagcccgaca cccagcttcg gtcagagaaa    240
tgagagggaa agtaaaaatg cgtcgagctc tgaggagagc ccccgcttct acccgcgcct    300
cttcccggca gccgaacccc aaacagccac ccgccaggat gccgcctcct cactcaccca    360
ctcgccaccg cctgcgcctc cgccgccgcg ggcgcaggca ccgcaaccgc agccccgccc    420
cgggcccgcc ccgggcccg ccccgaccac gccccggccc cggccccggc cccggcccccg    480
gcccctagcg cgcgactcct gagttccaga gcttgctaca ggctgcggtt gtttccctcc    540
ttgttttctt ctggttaatc tttatcaggt cttttcttgt tcaccctcag cgagtactgt    600
gagagcaagt agtggggaga gagggtggga aaaacaaaaa cacacacctc ctaaacccac    660
acctgctctt gctagacccc gccccaaaa gagaagcaac cgggcagcag ggacggctga    720
cacaccaagc gtcatctttt acgtgggcgg aacttgtcgc tgtttgacgc acctctcttt    780
cct                                                                 783
```

<210> SEQ ID NO 14
<211> LENGTH: 45
<212> TYPE: DNA
<213> ORGANISM: Artificial sequence
<220> FEATURE:
<223> OTHER INFORMATION: Primer

<400> SEQUENCE: 14

```
cgactggagc acgaggacac tgaaaagatg acgcttggtg tgtca                     45
```

<210> SEQ ID NO 15
<211> LENGTH: 21
<212> TYPE: DNA
<213> ORGANISM: Artificial sequence
<220> FEATURE:
<223> OTHER INFORMATION: Primer

<400> SEQUENCE: 15

```
cccacacctg ctcttgctag a                                               21
```

<210> SEQ ID NO 16
<211> LENGTH: 22
<212> TYPE: DNA
<213> ORGANISM: Artificial sequence
<220> FEATURE:
<223> OTHER INFORMATION: Primer

<400> SEQUENCE: 16

```
cgactggagc acgaggacac tg                                              22
```

<210> SEQ ID NO 17
<211> LENGTH: 23
<212> TYPE: DNA
<213> ORGANISM: Artificial sequence
<220> FEATURE:
<223> OTHER INFORMATION: Probe

<400> SEQUENCE: 17

```
cccaaaagag aagcaaccgg gca                                             23
```

```
<210> SEQ ID NO 18
<211> LENGTH: 38
<212> TYPE: DNA
<213> ORGANISM: Artificial sequence
<220> FEATURE:
<223> OTHER INFORMATION: Primer

<400> SEQUENCE: 18
cgactggagc acgaggacac tgacggctgc cgggaaga                              38

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
agaaatgaga gggaaagtaa aaatgc                                            26

<210> SEQ ID NO 20
<211> LENGTH: 22
<212> TYPE: DNA
<213> ORGANISM: Artificial sequence
<220> FEATURE:
<223> OTHER INFORMATION: Primer

<400> SEQUENCE: 20
cgactggagc acgaggacac tg                                                22

<210> SEQ ID NO 21
<211> LENGTH: 23
<212> TYPE: DNA
<213> ORGANISM: Artificial sequence
<220> FEATURE:
<223> OTHER INFORMATION: Probe

<400> SEQUENCE: 21
aggagagccc ccgcttctac ccg                                               23

<210> SEQ ID NO 22
<211> LENGTH: 42
<212> TYPE: DNA
<213> ORGANISM: Artificial sequence
<220> FEATURE:
<223> OTHER INFORMATION: Primer

<400> SEQUENCE: 22
cgactggagc acgaggacac tgacgctgag ggtgaacaag aa                          42

<210> SEQ ID NO 23
<211> LENGTH: 21
<212> TYPE: DNA
<213> ORGANISM: Artificial sequence
<220> FEATURE:
<223> OTHER INFORMATION: Primer

<400> SEQUENCE: 23
gagttccaga gcttgctaca g                                                 21

<210> SEQ ID NO 24
<211> LENGTH: 22
<212> TYPE: DNA
<213> ORGANISM: Artificial sequence
<220> FEATURE:
<223> OTHER INFORMATION: Primer
```

```
<400> SEQUENCE: 24
cgactggagc acgaggacac tg                                           22

<210> SEQ ID NO 25
<211> LENGTH: 24
<212> TYPE: DNA
<213> ORGANISM: Artificial sequence
<220> FEATURE:
<223> OTHER INFORMATION: Probe

<400> SEQUENCE: 25
ctgcggttgt ttccctcctt gttt                                         24

<210> SEQ ID NO 26
<211> LENGTH: 20
<212> TYPE: DNA
<213> ORGANISM: Artificial sequence
<220> FEATURE:
<223> OTHER INFORMATION: Primer

<400> SEQUENCE: 26
ggcaaattca acggcacagt                                              20

<210> SEQ ID NO 27
<211> LENGTH: 20
<212> TYPE: DNA
<213> ORGANISM: Artificial sequence
<220> FEATURE:
<223> OTHER INFORMATION: Primer

<400> SEQUENCE: 27
gggtctcgct cctggaagat                                              20

<210> SEQ ID NO 28
<211> LENGTH: 27
<212> TYPE: DNA
<213> ORGANISM: Artificial sequence
<220> FEATURE:
<223> OTHER INFORMATION: Probe

<400> SEQUENCE: 28
aaggccgaga atgggaagct tgtcatc                                      27

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tagtgcggac ctacccacga                                              20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ggtgtgtcag ccgtccctgc                                              20

<210> SEQ ID NO 31
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
gtgtcagccg tccctgctgc                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32 tgttttteee accctctctc                                               20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
ttttcccacc ctctctcccc                                               20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
tcccaccctc tctccccact                                               20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
caccctctct ccccactact                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
gagggtgaac aagaaaagac                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
```

-continued gaaaagacct gataaagatt                                       20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
agattaacca gaagaaaaca                                       20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ttaaccagaa gaaaacaagg                                       20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
accagaagaa aacaaggagg                                       20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
agaagaaaac aaggagggaa                                       20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42 agaaacaag gagggaaaca                                        20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
aaacaaggag ggaaacaacc                                       20

<210> SEQ ID NO 44
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 44
gcaagctctg gaactcagga                                                20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
agctctggaa ctcaggagtc                                                20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
tcaggagtcg cgcgctaggg                                                20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
ggagtcgcgc gctaggggcc                                                20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
gtcgcgcgct aggggccggg                                                20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
gcgcgctagg ggccggggcc                                                20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gggctgcggt tgcggtgcct                                                20
```

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
gcggttgcgg tgcctgcgcc                                        20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tgcggtgcct gcgcccgcgg                                        20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tgcctgcgcc cgcggcggcg                                        20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
gcgcccgcgg cggcggaggc                                        20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
cgcggcggcg gaggcgcagg                                        20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
cggcggaggc gcaggcggtg                                        20

<210> SEQ ID NO 57
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 57
gaggcgcagg cggtggcgag                                                   20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
gcaggcggtg gcgagtgggt                                                   20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
cggtggcgag tgggtgagtg                                                   20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
gcgagtgggt gagtgaggag                                                   20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
tgggtgagtg aggaggcggc                                                   20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
gagtgaggag gcggcatcct                                                   20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
aggaggcggc atcctggcgg                                                   20

```
<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
gcggcatcct ggcgggtggc                                                    20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
atcctggcgg gtggctgttt                                                    20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
tcggctgccg ggaagaggcg                                                    20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
tgccgggaag aggcgcgggt                                                    20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
ggaagaggcg cgggtagaag                                                    20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
gctctcctca gagctcgacg                                                    20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 70
cctcagagct cgacgcattt                                               20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gagctcgacg cattttact                                                20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
cgacgcattt ttactttccc                                               20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73 cattttact ttccctctca                                                20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
ttactttccc tctcatttct                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
ttccctctca tttctctgac                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
tctcatttct ctgaccgaag                                               20

<210> SEQ ID NO 77
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 77
tttctctgac cgaagctggg                                                    20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
ctgaccgaag ctgggtgtcg                                                    20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
cgaagctggg tgtcgggctt                                                    20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 80
ctgggtgtcg ggctttcgcc                                                    20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
tgtcgggctt tcgcctctag                                                    20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
ggctttcgcc tctagcgact                                                    20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
```

```
<223> OTHER INFORMATION: I
<220> FEATURE:
<221> NAME/KEY: modified_base
<222> LOCATION: (10)..(10)
<223> OTHER INFORMATION: I
<220> FEATURE:
<221> NAME/KEY: modified_base
<222> LOCATION: (15)..(15)
<223> OTHER INFORMATION: I

<400> SEQUENCE: 83
ccggggccgg ggccggggcc                                        20

<210> SEQ ID NO 84
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (13)..(13)
<223> OTHER INFORMATION: I

<400> SEQUENCE: 84
ggccggggcc ggggccgg                                          18

<210> SEQ ID NO 85
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 85
ggggccgggg ccggggcc                                          18

<210> SEQ ID NO 86
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 86
cggggccggg gccggggc                                          18

<210> SEQ ID NO 87
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 87
ccggggccgg ggccgggg                                          18

<210> SEQ ID NO 88
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 88
```

```
gccggggccg gggccggg                                                 18

<210> SEQ ID NO 89
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 89
ggccggggcc ggggccgg                                                 18

<210> SEQ ID NO 90
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 90
gggccggggc cggggccg                                                 18

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
ggccggggcc ggggcc                                                   16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
gggccggggc cggggc                                                   16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
ggggccgggg ccgggg                                                   16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
cggggccggg gccggg                                                   16

<210> SEQ ID NO 95
<211> LENGTH: 16
<212> TYPE: DNA
```

```
<213> ORGANISM: Artificial sequence
<220> FEATURE:
<223> OTHER INFORMATION: Synthetic oligonucleotide

<400> SEQUENCE: 95
ccggggccgg ggccgg                                                          16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
gccggggccg gggccg                                                          16

<210> SEQ ID NO 97
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 97
gacaagggta cgtaatctgt c                                                    21

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4)..(4)
<220> FEATURE:
<221> NAME/KEY: modified_base
<222> LOCATION: (10)..(10)
<220> FEATURE:
<221> NAME/KEY: modified_base
<222> LOCATION: (16)..(16)

<400> SEQUENCE: 98
ccggggccgg ggccggggcc                                                      20

<210> SEQ ID NO 99
<211> LENGTH: 18
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: I
<220> FEATURE:
<221> NAME/KEY: modified_base
<222> LOCATION: (12)..(12)
<223> OTHER INFORMATION: I

<400> SEQUENCE: 99
ggccggggcc ggggccgg                                                        18

<210> SEQ ID NO 100
<211> LENGTH: 19
<212> TYPE: DNA
<213> ORGANISM: Artificial sequence
<220> FEATURE:
```

<223> OTHER INFORMATION: Synthetic oligonucleotide

<400> SEQUENCE: 100
cagcagcagc agcagcagc                                                    19

<210> SEQ ID NO 101
<211> LENGTH: 99
<212> TYPE: DNA
<213> ORGANISM: Artificial sequence
<220> FEATURE:
<223> OTHER INFORMATION: Synthetic oligonucleotide

<400> SEQUENCE: 101
gacaagggta cgtaatctgt ctagagctag aaatagcaag ttaaaataag gctagtccgt        60
tatcaacttg aaaaagtggc accgagtcgg tgcttttt                                99

<210> SEQ ID NO 102
<211> LENGTH: 43
<212> TYPE: DNA
<213> ORGANISM: Artificial sequence
<220> FEATURE:
<223> OTHER INFORMATION: Primer

<400> SEQUENCE: 102
tagtcctgca ggtttaaacg aattcgtgag tgaggaggcg gca                          43

<210> SEQ ID NO 103
<211> LENGTH: 37
<212> TYPE: DNA
<213> ORGANISM: Artificial sequence
<220> FEATURE:
<223> OTHER INFORMATION: Primer

<400> SEQUENCE: 103
agcagagctc agattacgta cccttgttgt gaacaac                                 37

<210> SEQ ID NO 104
<211> LENGTH: 33
<212> TYPE: DNA
<213> ORGANISM: Artificial sequence
<220> FEATURE:
<223> OTHER INFORMATION: Primer

<400> SEQUENCE: 104
caatgtcaac gtctggcatt acttctactt ttg                                     33

<210> SEQ ID NO 105
<211> LENGTH: 43
<212> TYPE: DNA
<213> ORGANISM: Artificial sequence
<220> FEATURE:
<223> OTHER INFORMATION: Primer

<400> SEQUENCE: 105
tagggcgaat tgaatttagc ggccgcactg gcaggatcat agc                          43

<210> SEQ ID NO 106
<211> LENGTH: 30
<212> TYPE: DNA
<213> ORGANISM: Artificial sequence
<220> FEATURE:
<223> OTHER INFORMATION: Primer

<400> SEQUENCE: 106
tacgtaatct gagctctgct tatatagacc                                         30

```
<210> SEQ ID NO 107
<211> LENGTH: 42
<212> TYPE: DNA
<213> ORGANISM: Artificial sequence
<220> FEATURE:
<223> OTHER INFORMATION: Primer

<400> SEQUENCE: 107
aatgccagac gttgacattg attattgact agttattaat ag            42

<210> SEQ ID NO 108
<211> LENGTH: 23
<212> TYPE: DNA
<213> ORGANISM: Artificial sequence
<220> FEATURE:
<223> OTHER INFORMATION: Primer

<400> SEQUENCE: 108
gttaggctct gggagagtag ttg                                 23

<210> SEQ ID NO 109
<211> LENGTH: 21
<212> TYPE: DNA
<213> ORGANISM: Artificial sequence
<220> FEATURE:
<223> OTHER INFORMATION: Primer

<400> SEQUENCE: 109
cctggagcag gtaaatgctg g                                   21
```